United States Patent
Peyman et al.

(10) Patent No.: US 6,747,016 B1
(45) Date of Patent: Jun. 8, 2004

(54) SUBSTITUTED PURINE DERIVATIVES AS INHIBITORS OF CELL ADHESION

(75) Inventors: Anuschirwan Peyman, Kelkheim (DE); Jochen Knolle, Frankfurt am Main (DE); Thomas R Gadek, Oakland, CA (US); Jean-Francois Gourvest, Clave Souilly (FR); Jean-Marie Ruxer, Issy Les Moulineaux (FR)

(73) Assignees: Aventis Pharma Deutschland GmbH (DE); Genetech Inc.

( * ) Notice: Subject to any disclaimer, the term of this patent is extended or adjusted under 35 U.S.C. 154(b) by 0 days.

(21) Appl. No.: 10/030,290

(22) PCT Filed: Jun. 26, 2000

(86) PCT No.: PCT/EP00/05921

§ 371 (c)(1),
(2), (4) Date: Mar. 6, 2002

(87) PCT Pub. No.: WO01/02399

PCT Pub. Date: Jan. 11, 2001

(30) Foreign Application Priority Data

Jul. 2, 1999 (EP) .............................. 99112637

(51) Int. Cl.$^7$ .................. C07D 473/34; C07D 473/00; A61K 31/52; A61K 31/522; A61P 19/10

(52) U.S. Cl. .................. 514/81; 514/245; 514/248; 514/263.2; 514/263.21; 514/263.22; 514/263.3; 514/263.38; 544/276; 544/277; 544/264; 544/244; 544/198; 544/258

(58) Field of Search .............. 544/244, 198, 544/258, 264, 276, 277; 514/81, 245, 248, 263.2, 263.21, 263.22, 263.3, 263.38, 263.1

(56) References Cited

FOREIGN PATENT DOCUMENTS

| | | |
|---|---|---|
| EP | 0853084 | 7/1998 |
| WO | 9532710 | 12/1995 |
| WO | 9808840 | 3/1998 |
| WO | 9818461 | 5/1998 |
| WO | 9831359 | 7/1998 |
| WO | 9938621 | 7/1999 |

Primary Examiner—Mark L Berch
(74) Attorney, Agent, or Firm—Muserlian, Lucas and Mercanti

(57) ABSTRACT

The present invention relates to compounds of formula (I), in which B, D, E, G, X, Y, Z, R$^1$, R$^2$ and s have the meanings indicated in the claims, their physiologically tolerable salts and their prodrugs. The compounds of formula (I) are valuable pharmacologically active compounds. They are vitronectin receptor antagonist and inhibitors of cell adhesion and are suitable for the therapy and prophylaxis of illnesses which are based on the interaction between vitronectin receptors and their ligands in cell-cell or cell-matrix interaction processes or which can be prevented, alleviated or cured by influencing such interactions. For example, they can be applied for inhibiting bone resorption by osteoclasts and thus for treating and preventing osteoporosis, or for inhibiting undesired angiogenesis or proliferation of cells of the vascular smooth musculature. The invention furthermore relates to processes for the preparation of compounds of formula (I), their use, in particular as active ingredients in pharmaceuticals, and pharmaceutical compositions comprising them.

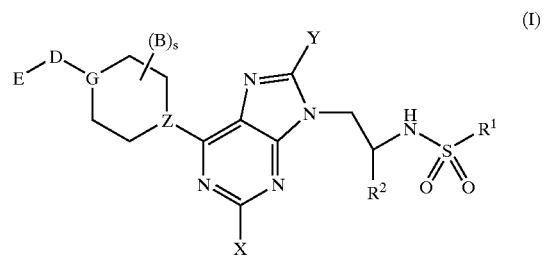

8 Claims, No Drawings

SUBSTITUTED PURINE DERIVATIVES AS INHIBITORS OF CELL ADHESION

This application is a 371 of PCT/EP00/05921 filed Jun. 26, 2000.

The present invention relates to compounds of the formula I,

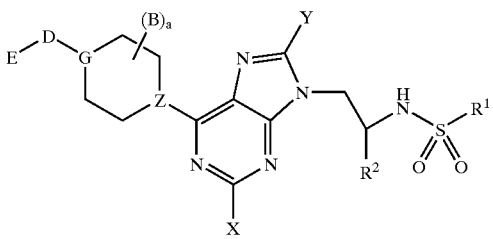

in which B, D, E, G, X, Y, Z, $R^1$, $R^2$ and s have the meanings indicated below, their physiologically tolerable salts and their prodrugs. The compounds of the formula I are valuable pharmacologically active compounds. They are vitronectin receptor antagonists and inhibitors of cell adhesion and are suitable for the therapy and prophylaxis of illnesses which are based on the interaction between vitronectin receptors and their ligands in cell-cell or cell-matrix interaction processes or which can be prevented, alleviated or cured by influencing such interactions. For example, they can be applied for inhibiting bone resorption by osteoclasts and thus for treating and preventing osteoporosis, or for inhibiting undesired angiogenesis or proliferation of cells of the vascular smooth musculature. The invention furthermore relates to processes for the preparation of compounds of the formula I, their use, in particular as active ingredients in pharmaceuticals, and pharmaceutical compositions comprising them.

Human bones are subject to a constant dynamic renovation process comprising bone resorption and bone formation. These processes are controlled by types of cell specialized for these purposes. Bone resorption is based on the destruction of bone matrix by osteoclasts. The majority of bone disorders are based on a disturbed equilibrium between bone formation and bone resorption. Osteoporosis is a disease characterized by low bone mass and enhanced bone fragility resulting in an increased risk of fractures. It results from a deficit in new bone formation versus bone resorption during the ongoing remodelling process. Conventional osteoporosis treatment includes, for example, the administration of bisphosphonates, estrogens, estrogen/progesterone (hormone replacement therapy or HRT), estrogen agonists/antagonists (selective estrogen receptor modulators or SERMs), calcitonin, vitamin D analogues, parathyroid hormone, growth hormone secretagogues, or sodium fluoride (Jardine et al., Annual Reports in Medicinal Chemistry 31 (1996) 211).

Activated osteoclasts are polynuclear cells having a diameter of up to 400 µm, which remove bone matrix. Activated osteoclasts become attached to the surface of the bone matrix and secrete proteolytic enzymes and adds into the so-called "sealing zone", the region between their cell membrane and the bone matrix. The acidic environment and the proteases cause the destruction of the bone. The compounds of the formula I inhibit bone resorption by osteoclasts.

Studies have shown that the attachment of osteoclasts to the bones is controlled by integrin receptors on the cell surface of osteoclasts. Integrins are a superfamily of receptors which include, inter alia, the fibrinogen receptor $\alpha_{IIb}\beta_3$ on the blood platelets and the vitronectin receptor $\alpha_v\beta_3$. The vitronectin receptor $\alpha_v\beta_3$ is a membrane glycoprotein which is expressed on the cell surface of a number of cells such as endothelial cells, cells of the vascular smooth musculature, osteoclasts and tumor cells. The vitronectin receptor $\alpha_v\beta_3$, which is expressed on the osteoclast membrane, controls the process of attachment to the bones and bone resorption and thus contributes to osteoporosis. $\alpha_v\beta_3$ in this case binds to bone matrix proteins such as osteopontin, bone sialoprotein and thrombospontin which contain the tripeptide motif Arg-Gly-Asp (or RGD).

Horton and coworkers describe RGD peptides and an anti-vitronectin receptor antibody (23C6) which inhibit tooth destruction by osteoclasts and the migration of osteoclasts (Horton et al., Exp. Cell. Res. 195 (1991) 368). In J. Cell Biol. 111 (1990) 1713 Sato et al. describe echistatin, an RGD peptide from snake venom, as a potent inhibitor of bone resorption in a tissue culture and as an inhibitor of osteoclast adhesion to the bones. Fisher et al. (Endocrinology 132 (1993) 1411) and Yamamoto et al. (Endocrinology 139 (1998) 1411) were able to show in the rat that echistatin also inhibits bone resorption in vivo.

It was furthermore shown that the vitronectin $\alpha_v\beta_3$ on human cells of the vascular smooth musculature of the aorta stimulates the migration of these cells into the neointima which finally leads to arteriosclerosis and restenosis after angioplasty (Brown et al., Cardiovascular Res. 28 (1994) 1815). Yue et al. (Pharmacology Reviews and Communications 10 (1998) 9) show the inhibition of neointima formation using an $\alpha_v\beta_3$ antagonist.

Brooks et al. (Cell 79 (1994) 1157) showed that antibodies against $\alpha_v\beta_3$ or $\alpha_v\beta_3$ antagonists can cause a shrinkage of tumors by inducing the apoptosis of blood vessel cells during angiogenesis. The vitronectin receptor $\alpha_v\beta_3$ is also involved in the progression of a variety of other types of cancer, and is overexpressed in malignant melanoma cells (Engleman et al., Annual Reports in Medicinal Chemistry 31 (1996) 191). The melanoma invasiveness correlated with this overexpression (Stracke et al., Encylopedia of Cancer, volume III, 1855, Academic Press, 1997; Hillis et al., Clinical Science 91 (1996) 639). Carron et al. (Cancer Res. 58 (1998) 1930) describe the inhibition of tumor growth and the inhibition of hypercalcemia of malignancy using an $\alpha_v\beta_3$ antagonist.

Friedlander et al. (Science 270 (1995) 1500) describe anti-$\alpha_v\beta_3$ antibodies or $\alpha_v\beta_3$ antagonists which inhibit the bFGF-induced angiogenesis processes in the rat eye, a property which can be used therapeutically in the treatment of retinopathies and in the treatment of psoriasis. Storgard et al. (J. Clin. Invest. 103 (1999) 47) describe the use of avid antagonists in the treatment of arthritic diseases.

Influencing of the vitronectin receptor or of the interactions in which it is involved thus offers the possibility of influencing different disease states for whose therapy and prophylaxis there continues to be a need for suitable pharmaceutical active ingredients.

EP-A-528586 and EP-A-528587 disclose aminoalkyl-substituted or heterocyclyl-substituted phenylalanine derivatives, and WO-A-95/32710 discloses aryl derivatives as inhibitors of bone resorption by osteoclasts. In WO-95/28426 RGD peptides are described as inhibitors of bone resorption, angiogenesis and restenosis. International Patent Application PCT/EP98/08051 discloses carbamic ester derivatives, and International Patent Application PCT/EP99/00242 discloses sulfonamides which are vitronectin receptor antagonists. Further vitronectin receptor antagonists are disclosed in WO-A-98/08840 and WO-A-98/18461. Substituted purine derivatives as inhibitors of bone resorption are described in EP-A853084. Further investigations have shown that the compounds of the formula I are particularly strong inhibitors of the vitronectin receptor and of bone resorption by osteoclasts.

The present invention relates to compounds of the formula I,

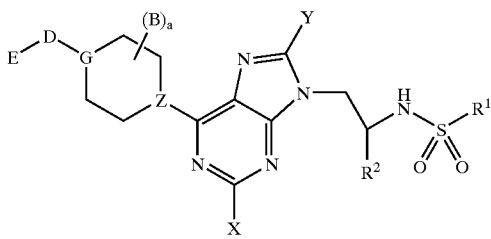

in which

- B is $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl, $(C_5-C_{14})$-heteroaryl-$(C_1-C_8)$-alkyl-, fluorine, chlorine, bromine, hydroxy, cyano, trifluoromethyl, nitro, hydroxycarbonyl-, $(C_1-C_6)$-alkoxy, $(C_1-C_6)$-alkoxy-$(C_1-C_6)$-alkyl-, $(C_1-C_6)$-alkoxycarbonyl-, $(C_1-C_6)$-alkylcarbonyl-, $(C_5-C_{14})$-arylcarbonyl-, $(C_1-C_6)$-alkylaminocarbonyl-, $(C_1-C_6)$-alkoxy-$(C_1-C_6)$-alkoxy-, $(C_5-C_{14})$-aryl-$(C_1-C_8)$-alkylcarbonyl-, $(C_1-C_6)$-alkanoylamino-, $(C_1-C_6)$-alkylsulfonylamino-, $(C_5-C_{14})$-arylsulfonylamino-, $(C_1-C_6)$-alkylamino-, di-$((C_1-C_6)$-alkyl)-amino-, $(C_1-C_6)$-alkylsulfonyl-, aminosulfonyl-, $(C_5-C_{14})$-arylsulfonyl-, $(C_5-C_{14})$-aryl-$(C_1-C_6)$-alkylsulfonyl-, $(C_5-C_{14})$-aryl or $(C_5-C_{14})$-heteroaryl, where all residues B are independent of one another and can be identical or different, or B denotes an aromatic or non-aromatic ring system that is fused to the 6-membered ring containing the groups G and Z;
- D is —C(O)—N($R^6$—C(O)—, —N$R^6$—C(O)—, —N$R^6$—C(O)—N($R^6$)—, —N$R^6$—C(S)—N($R^6$)—, —C(S)—N($R^6$)— or —C($R^6$)=N—N($R^6$)—, where the divalent residues representing D are bonded to the group E via the free bond on their right side;
- E is a residue from the series consisting of

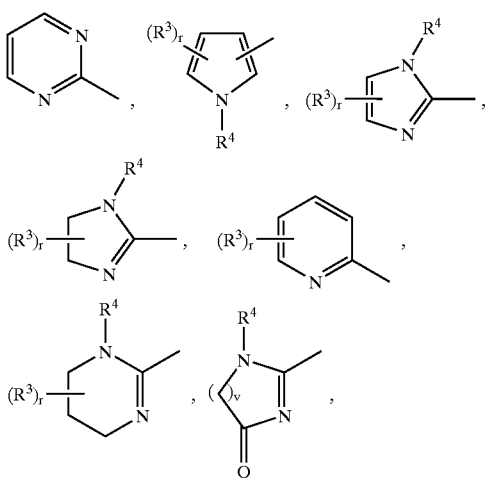

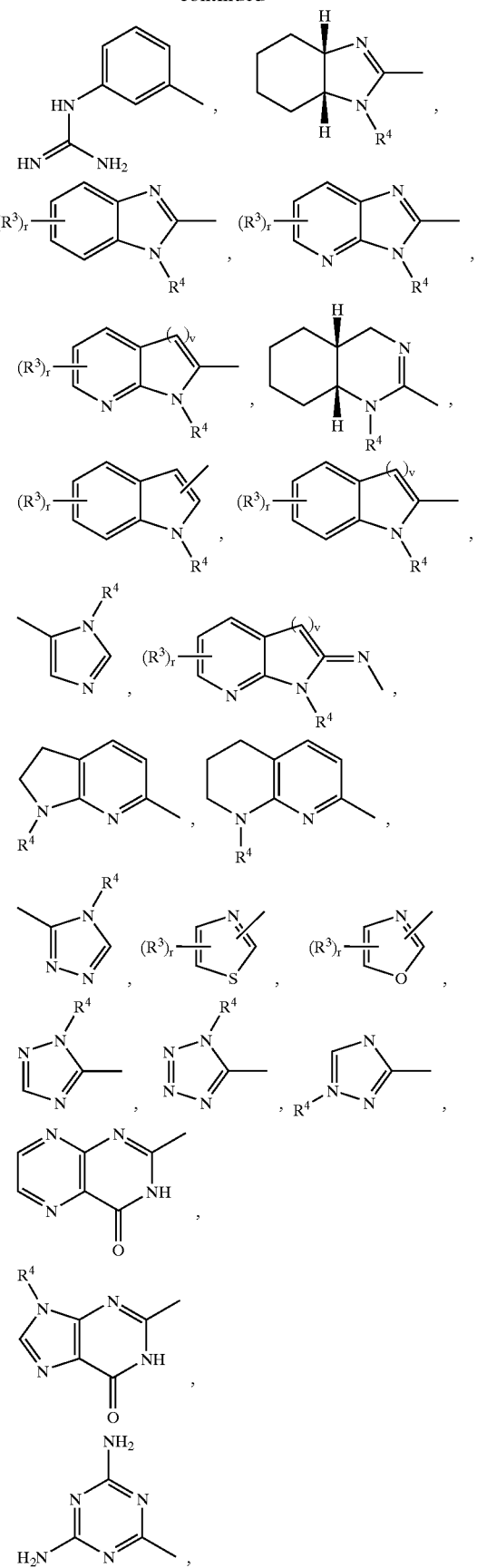

$R^6$—C(=NR$^6$)—NR$^6$— and $R^6R^{6'}$N—C(=NR$^6$)—;

G is N, CH or C(($C_1$–$C_4$)-alkyl);

X is hydrogen, —NR$^6$R$^{6'}$, fluorine, chlorine, bromine, —OR$^6$, —SR$^6_1$, hydroxy-($C_1$–$C_6$)-alkyl-NH—, (hydroxy-($C_1$–$C_6$)-alkyl)$_2$N—, amino-($C_1$–$C_6$)-alkyl-NH—, (amino-($C_1$–$C_6$)-alkyl)$_2$N—, hydroxy-($C_1$–$C_6$)-alkyl-O—, hydroxy-($C_1$–$C_6$)-alkyl-S— or —NH—C(O)—R$^6$;

Y has one of the meanings of R$^6$ or is fluorine, chlorine, bromine, cyano, —NR$^6$R$^{6'}$, —OR$^6$, —SR$^6$ or hydroxy-($C_1$–$C_6$)-alkyl-NH—;

Z is N or CH;

$R^1$ is ($C_1$–$C_{18}$)-alkyl, ($C_3$–$C_{14}$)-cycloalkyl, ($C_3$–$C_{14}$)-cycloalkyl-($C_1$–$C_8$)-alkyl-, ($C_5$–$C_{14}$)-aryl, ($C_5$–$C_{14}$)-aryl-($C_1$–$C_8$)-alkyl-, ($C_5$$C_4$)-heteroaryl or ($C_5$–$C_{14}$)-heteroaryl-($C_1$–$C_8$)-alkyl- where aryl, heteroaryl, cycloalkyl and alkyl can be substituted one, two or three times by identical or different substituents from the series consisting of fluorine, chlorine, bromine, cyano, trifluoromethyl, nitro, hydroxycarbonyl-, ($C_1$–$C_6$)-alkyl, ($C_1$–$C_6$)-alkoxy, ($C_1$–$C_6$)-alkoxy-($C_1$–$C_6$)-alkyl-, ($C_1$–$C_6$)-alkoxycarbonyl-, ($C_1$–$C_6$)-alkylcarbonyl-, ($C_1$–$C_6$)-alkylaminocarbonyl-, ($C_1$–$C_6$)-alkoxy-($C_1$–$C_6$)-alkoxy-, ($C_{56l}$–$C_{14}$)-arylcarbonyl-, ($C_5$–$C_{14}$)-aryl-($C_1$–$C_8$)-alkylcarbonyl-, ($C_1$–$C_6$)-alkanoylamino-, ($C_5$–$C_{14}$)-arylsulfonylamino-, ($C_1$–$C_6$)-alkylsulfonylamino-, ($C_1$–$C_6$)-alkylamino-, di-(($C_1$–$C_6$)-alkyl)-amino-, ($C_1$–$C_6$)-alkylsulfonyl-, ($C_1$–$C_6$)-alkylaminosulfonyl-, ($C_5$–$C_{14}$)-arylaminosulfonyl-, ($C_5$–$C_{14}$)-aryl-($C_1$–$C_8$)-alkylaminosulfonyl-, ($C_5$–$C_{14}$)-arylsulfonyl-, ($C_5$–$C_{14}$)-aryl-($C_1$–$C_8$)-alkylsulfonyl-, ($C_5$–$C_{14}$)-aryl and ($C_5$–$C_{14}$)-heteroaryl;

$R^2$ is —C(O)R$^5$, —C(S)R$^5$, —S(O)$_p$R$^5$, —P(O)R$^5$R$^{5'}$ or a residue of a 4-membered to 8-membered saturated or unsaturated heterocycle which contains 1, 2, 3 or 4 heteroatoms from the series consisting of nitrogen, oxygen and sulfur;

$R^3$ is ($C_1$–$C_{18}$)-alkyl, ($C_3$–$C_{14}$)-cycloalkyl, ($C_3$–$C_{14}$)-cycloalkyl-($C_1$–$C_8$)-alkyl-, ($C_5$–$C_{14}$)-aryl, ($C_{56l}$–$C_{14}$)-aryl-($C_1$–$C_8$)-alkyl-, ($C_5$–$C_{14}$)-heteroaryl, ($C_5$–$C_{14}$)-heteroaryl-($C_1$–$C_8$)-alkyl-, fluorine, chlorine, bromine, hydroxy, cyano, trifluoromethyl, nitro, hydroxycarbonyl-, ($C_1$–$C_6$)-alkoxy, ($C_1$–$C_6$)-alkoxy-($C_1$–$C_6$)-alkyl-, ($C_1$–$C_6$)-alkoxycarbonyl-, ($C_1$–$C_6$)-alkylcarbonyl-, ($C_5$–$C_{14}$)-arylcarbonyl-, ($C_1$–$C_6$)-alkylaminocarbonyl-, ($C_1$–$C_6$)-alkoxy-($C_1$–$C_6$)-alkoxy-, ($C_6$–$C_{14}$)-aryl-($C_1$–$C_8$)-alkylcarbonyl-, ($C_1$–$C_6$)-alkanoylamino-, ($C_1$–$C_6$)-alkylsulfonylamino-, ($C_5$–$C_{14}$)-arylsulfonylamino-, ($C_1$–$C_6$)-alkylamino-, di-(($C_1$–$C_6$)-alkyl)-amino-, ($C_1$–$C_6$)-alkylsulfonyl-, aminosulfonyl-, ($C_5$–$C_{14}$)-arylsulfonyl-, ($C_5$–$C_4$)-aryl-($C_1$–$C_5$)-alkylsulfonyl-, ($C_5$–$C_{14}$)-aryl or ($C_5$–$C_{14}$)-heteroaryl, where all residues R$^3$ are independent of one another and can be identical or different;

$R^4$ is hydrogen, ($C_1$–$C_{10}$)-alkyl, ($C_3$–$C_{14}$)-cycloalkyl, ($C_3$–$C_{14}$)-cycloalkyl-($C_1$–$C_8$)-alkyl-, ($C_5$$C_4$)-aryl or ($C_5$–$C_{14}$)-aryl-($C_1$–$C_8$)-alkyl-;

$R^5$ and $R^{5'}$ are hydroxy, ($C_1$–$C_8$)-alkoxy, ($C_5$–$C_{14}$)-aryl-($C_1$–$C_8$)-alkoxy-, ($C_1$–$C_8$)-alkylcarbonyloxy-($C_1$–$C_4$)-alkoxy-, ($C_5$–$C_{14}$)-aryl-($C_1$–$C_8$)-alkylcarbonyloxy-($C_1$–$C_8$)-alkoxy- or —NR$^6$R$^{6'}$, where the residues R$^5$ and R$^{5'}$ are independent of one another and can be identical or different;

$R^6$ and $R^{6'}$ are hydrogen, ($C_1$–$C_{18}$)-alkyl, ($C_3$–$C_{14}$)-cycloalkyl, ($C_3$–$C_{14}$)-cycloalkyl-($C_1$–$C_8$)-alkyl-, ($C_5$–$C_{14}$)-aryl where in the aryl residue one, two, three, four or five ring carbon atoms can be replaced by heteroatoms from the series consisting of nitrogen, oxygen and sulfur, or ($C_5$–$C_{14}$)-aryl-($C_1$–$C_5$)-alkyl- where in the aryl moiety of the aryl-alkyl-residue one, two, three, four or five ring carbon atoms can be replaced by heteroatoms from the series consisting of nitrogen, oxygen and sulfur, or R$^6$ and R$^{6'}$ together with the nitrogen atom to which they are bonded form a 4-membered to 8-membered ring system which in addition to the nitrogen atom to or which R$^6$ and R$^{6'}$ are bonded can contain one, two or three ring heteroatoms from the series consisting of nitrogen, oxygen and sulfur and which can be unsaturated or saturated, where all residues R$^6$ and R$^{6'}$ are independent of one another and can be identical or different;

r is zero, one, two, three or four;

s is zero, one, two, three or four;

v is one, two or three;

p is one or two;

in all their stereoisomeric forms and mixtures thereof in all ratios, and their physiologically tolerable salts and their prodrugs;

where, instead of the purine structure shown in formula I, also a 3deazapurine structure, a 7-deazapurine structure or a 7-deaza-8-azapurine structure can be present.

All residues and numbers (or indices) which can occur several times in the compounds of the formula I, for example the residues B, R$^3$, R$^6$, R$^{6'}$ but also all other residues to which this applies, can each independently of one another have the meanings indicated. They can all be identical or different likewise, heteroatoms in heterocyclic rings or substituents in residues which can be present several times can in each case independently of one another have the meanings indicated and can all be identical or different.

Alkyl residues can be straight-chain or branched and can be saturated or mono-unsaturated or poly-unsaturated. This also applies if they carry substituents or occur as substituents on other residues, for example in alkoxy residues, alkoxycarbonyl residues or arylalkyl residues. Substituted alkyl residues can be substituted in any suitable position. Examples of alkyl residues containing from 1 to 18 carbon atoms are methyl, ethyl, propyl, butyl, pentyl, hexyl, heptyl, octyl, nonyl, decyl, undecyl, dodecyl, tetradecyl, hexadecyl and octadecyl, the n-isomers of all these residues, isopropyl, isobutyl, isopentyl, neopentyl, isohexyl, isodecyl, 3-methylpentyl, 2,3,4-trimethylhexyl, sec-butyl, tert-butyl, or tert-pentyl. A preferred group of alkyl residues is formed by the residues methyl, ethyl, n-propyl, isopropyl, n-butyl, isobutyl, sec-butyl and tert-butyl.

Unsaturated alkyl residues can contain one or more, for example one, two or three, double bonds and/or triple bonds. Of course, an unsaturated alkyl residue has to have at least two carbon atoms. Examples of unsaturated alkyl residues are alkenyl residues such as vinyl, 1-propenyl, allyl, butenyl or 3-methyl-2-butenyl, or alkynyl residues such as ethynyl, 1-propynyl or propargyl. Alkyl residues can also be unsaturated when they are substituted. Preferably an unsaturated alkyl residue is mono-unsaturated and contains one double bond or triple bond.

These statements relating to alkyl residues correspondingly apply to residues which may be regarded as divalent or polyvalent alkyl residues, for example the alkyl moiety in a substituted alkyl residue like hydroxy-alkyl-. The bonds via which the substituents in a substituted alkyl residue are attached to the alkyl moiety and the bond via which the alkyl moiety is attached to its neighbouring group can be located in any desired positions.

Cycloalkyl residues can be monocyclic, bicyclic or tricyclic, i. e., they can be monocycloalkyl residues, bicycloalkyl residues and tricycloalkyl residues, provided they have a suitable number of carbon atoms and the parent hydrocarbons are stable. A bicylic or tricyclic cycloalkyl residue has to have at least 4 carbon atoms. Preferably a bicyclic or tricyclic cycloalkyl residue has at least 5 carbon atoms, more preferably at least 6 carbon atoms, and up to the number of carbon atoms specified in the respective definition. Thus, $(C_3-C_{14})$-cycloalkyl comprises but is not limited to, for example, $(C_3-C_{14})$-monocycloalkyl, $(C_6-C_{14})$-bicycloalkyl and $(C_6-C_{14})$-tricycloalkyl, and $(C_3-C_{12})$-cycloalkyl comprises but is not limited to, for example, $(C_3-C_{12})$-monocycloalkyl, $(C_6-C_{12})$-bicycloalkyl and $(C_6-C_{12})$-tricycloalkyl.

Monocycloalkyl residues are, for example, cyclopropyl, cyclobutyl, cyclopentyl, cyclohexyl, cycloheptyl, cyclooctyl, cyclononyl, cyclodecyl, cycloundecyl, cyclododecyl or cyclotetradecyl which can also be substituted by, for example, $(C_1-C_4)$-alkyl. Examples of substituted cycloalkyl residues which may be mentioned are 4-methylcyclohexyl and 2,3-dimethylcyclopentyl.

Bicycloalkyl residues and tricycloalkyl residues can likewise be unsubstituted or substituted in any desired suitable position, for example by one or more oxo groups and/or one or more identical or different $(C_1-C_4)$-alkyl groups, for example methyl or isopropyl groups, preferably methyl groups. The bond via which the bicyclic or the tricyclic residue is bonded can be located in any desired position in the molecule; the residue can thus be bonded via a bridgehead atom or an atom in a bridge. The bond via which the residue is bonded can also be located in any desired stereochemical position, for example in an exo-position or an endo-position.

Examples of parent structures of bicyclic ring systems are norbomane (=bicyclo[2.2.1]heptane), bicyclo[2.2.2]octane and bicyclo[3.2.1]octane. An example of a system substituted by an oxo group is camphor (=1,7,7-trimethyl-2-oxobicyclo[2.2.1]heptane). Examples of parent structures of tricyclic systems are twistane (=tricyclo[4.4.0.0$^{3,8}$]decane), adamantane (=tricyclo[3.3.1.1$^{3,7}$]decane), noradamantane (=tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,9}$]undecane or tricyclo[5.5.1.0$^{3,11}$]tridecane. A residue derived from adamantane can be 1-adamantyl or 2-adamantyl.

$(C_5-C_{14})$-Aryl includes heterocyclic $(C_5-C_{14})$-aryl residues (=$(C_5-C_{14})$-heteroaryl residues) in which one or more of the 5 to 14 ring carbon atoms are replaced by heteroatoms such as nitrogen, oxygen or sulfur, and carbocyclic $(C_6-C_{14})$-aryl residues. Examples of carbocyclic $(C_6-C_{14})$-aryl residues are phenyl, naphthyl such as 1-naphthyl or 2-naphthyl, biphenylyl such as 2-biphenylyl, 3-biphenylyl or 4-biphenylyl, anthryl or fluorenyl, where $(C_6-C_{12})$-aryl residues, in particular 1-naphthyl, 2-naphthyl and phenyl, are preferred. If not stated otherwise, aryl residues, in particular phenyl residues, can be unsubstituted or substituted by one or more, preferably one, two or three, identical or different substituents. In particular substituted aryl residues can be substituted by identical or different residues from the series consisting of $(C_1-C_8)$-alkyl, in particular $(C_1-C_4)$-alkyl, $(C_1-C_8)$-alkoxy, in particular $(C_1-C_4)$-alkoxy, fluorine, chlorine and bromine, nitro, amino, $(C_1-C_4)$-alkylamino, di-$((C_1-C_4)$-alkyl)-amino, trifluoromethyl, hydroxy, methylenedioxy, cyano, hydroxycarbonyl-, aminocarbonyl-, $(C_1-C_4)$-alkoxycarbonyl-, phenyl, phenoxy, benzyl, benzyloxy, tetrazolyl, $(R^9O)_2P(O)-$ and $(R^9O)_2P(O)O-$ where $R^9$ is hydrogen, $(C_1-C_{10})$-alkyl, $(C_6-C_{14})$-aryl or $(C_6-C_{14})$-aryl-$(C_1-C_8)$-alkyl. In general, only up to two nitro groups can be present in the compounds of formula I, and similarly all other groups, substituents or heteroatoms mentioned in the definition of the compounds of formula I can only be present in the compounds of formula I in such positions and in such numbers and in such combinations that the resulting molecule is stable and does not exhibit characteristics that are not desired for the intended use.

In monosubstituted phenyl residues the substituent can be located in the 2-position, the 3-position or the 4-position, the 3-position and the 4-position being preferred. If phenyl is disubstituted, the substituents can be in 2,3-position, 2,4-position, 2,5-position, 2,6-position, 3,4-position or 3,5-position. Preferably in disubstituted phenyl residues the two substituents are located in 3,4-position relative to the linkage site. In trisubstituted phenyl residues, the substituents can be in 2,3,4-position, 2,3,5-position, 2,3,6-position, 2,4,5-position, 2,4,6-position or 3,4,5-position. Similarly, naphthyl residues and other aryl residues can be substituted in any desired position, for example a 1-naphthyl residue in the 2-, 3-, 4-, 5-, 6-, 7- and 8-position, 2-naphthyl residue in the 1-, 3-, 4-, 5-, 6-, 7- and 8-position.

Beside carbocyclic systems, $(C_5-C_{14})$-aryl groups can also be monocyclic or polycyclic, for example monocyclic, bicyclic or tricyclic, aromatic ring systems in which 1, 2, 3, 4 or 5 ring carbon atoms are replaced by heteroatoms, in particular by identical or different heteroatoms from the series consisting of nitrogen, oxygen and sulfur. Examples of heterocyclic $(C_5-C_{14})$-aryl groups and $(C_5-C_{14})$-heteroaryl groups are pyridyl like 2-pyridyl, 3-pyridyl and 4-pyridyl, pyrrolyl like 2-pyrrolyl and 3-pyrrolyl, furyl like 2-furyl and 3-furyl, thienyl like 2-thienyl and 3-thienyl, imidazolyl, pyrazolyl, oxazolyl, isoxazolyl, thiazolyl, isothiazolyl, tetrazolyl, pyridazinyl, pyrazinyl, pyrimidinyl, indolyl, isoindolyl, indazolyl, phthalazinyl, quinolyl, isoquinolyl, quinoxalinyl, quinazolinyl, cinnotinyl, β-carbolinyl, or benzo-fused, cyclopenta-fused, cyclohexa-fused or cyclohepta-fused derivatives of these residues. The heterocyclic systems can be substituted in any suitable position by the substituents listed above with respect to carbocyclic aryl systems.

In the series of these heteroaryl groups, monocyclic or bicyclic aromatic ring systems which have 1, 2 or 3 ring heteroatoms, in particular 1 or 2 ring heteroatoms, from the series consisting of nitrogen, oxygen and sulfur and which can be unsubstituted or substituted by 1, 2 or 3 substituents from the series consisting of $(C_1-C_6)$-alkyl, $(C_1-C_6)$-alkoxy, fluorine, chlorine, nitro, amino, trifluoromethyl, hydroxy, $(C_1-C_4)$-alkoxycarbonyl-, phenyl, phenoxy, benzyloxy and benzyl, are preferred. Particularly preferred here are monocyclic or bicyclic aromatic 5-membered to 10-membered ring systems having 1, 2 or 3 heteroatoms, in particular having 1 or 2 ring heteroatoms, from the series consisting of nitrogen, oxygen and sulfur which can be substituted by 1 to 2 substituents from the series consisting of $(C_1-C_4)$-alkyl, $(C_1-C_4)$-alkoxy, phenyl, phenoxy, benzyl and benyloxy. More particularly preferred are 5-membered or 6-membered monocyclic heteroaryl groups and 9-membered or 10-membered bicyclic heteroaryl groups containing 1 or 2, in particular 1, ring heteroatom from the series consisting of nitrogen, oxygen and sulfur which are unsubstituted or substituted as described before.

The above statements relating to aryl residues also correspondingly apply to the aryl moiety in groups like, for example, aryl-alkyl-. Examples of aryl-alkyl-residues which can also carry in the aryl moiety the substituents listed above, are benzyl, 1-phenylethyl or 2-phenylethyl.

In addition to the above-mentioned heteroaryl groups, as examples of saturated and unsaturated heterocyclic ring systems like 4-membered to 8-membered ring systems from which heterocyclic residues may be derived if they are in line with the definition of the respective group, there may be mentioned azetidine, tetrahydropyran, 1,4-dioxacyclohexane, morpholine, thiomorpholine, piperazine, piperidine, pyrrolidine, dihydroisoxazole, tetrahydroisoxazole, 1,3-dioxolane, 1,2-dithiolane, 2,3-dihydrofuran, 2,5-dihydrofuran, tetrahydrofuran, 2,3-dihydrothiophene, 2,5-dihydrothiophene, tetrahydrothiophene, 2-imidazoline, 3-imidazoline, 4-imidazoline, imidazolidine, 2-oxazoline, 3-oxazoline, 4-oxazoline, oxazolidine, 2-thiazoline, 3-thiazoline, 4-thiazoline, thiazolidine, 2H-thiapyran, 2H-pyran, 4H-pyran.

If in the formulae of an heterocyclic residue representing the group E the bond via which the residue is connected to the group D, and/or the bond via which substituents $R^3$ are connected to the residue, are not explicitly directed to a specific ring carbon atom but are drawn through a side of the ring this means that the bond via which the residue is connected to the group D and/or the bonds via which the substituents $R^3$ are connected can be located on any suitable ring carbon atom of the residue. Thus, for example, in the $1-(R^4)$-imidazol-2-yl residue and the $1-(R^4)$-4,5-dihydroimidazol-2-yl residue representing E the substituents $R^3$ can be present in the 4-position and/or in the 5-position, in the 1,4,5,6-tetrahydropyrimidin-2-yl residue representing E the substituents $R^3$ can be present in the 4-position and/or 5-position and/or 6-position, in the indolyl residue the substituents $R^3$ can be present on any suitable ring carbon atom and the indolyl residue can be bonded via any suitable ring carbon atom, preferably via the 2-position or the 3-position. A 1,3-oxazolyl residue or a 1,3-thiazolyl residue representing E can be 1,3-oxazol-2-yl, 1,3-oxazolyl, 1,3-oxazol-5-yl, 1,3thiazol-2-yl, 1,3-thiazol-4-yl, 1,3-thiazol-5-yl where the 2-yl residues are preferred, and in all these residues substituents $R^3$ can be present on any one or on both of the carbon atoms not bonded to the group D.

Optically active carbon atoms present in the compounds of the formula I can independently of one another have R configuration or S configuration. The compounds of the formula I can be present in the form of pure enantiomers or pure diastereomers or in the form of mixtures of enantiomers, for example in the form of racemates, or of mixtures of diastereomers. The present invention relates to both pure enantiomers and mixtures of enantiomers as well as to pure diastereomers and mixtures of diastereomers. The invention comprises mixtures of two or of more than two stereoisomers of the formula I, and it comprises all ratios of stereoisomers in the mixtures. Compounds of the formula I containing respective structural units can also be present as E isomers or Z isomers (or trans isomers or cis isomers). The invention relates to both pure E isomers, pure Z isomers, pure cis isomers, pure trans isomers and to E/Z mixtures and cis/trans mixtures in all ratios. The invention also comprises all tautomeric forms of the compounds of the formula I. Diastereomers, including E/Z isomers, can be separated into the individual isomers, for example, by chromatography. Racemates can be separated into the two enantiomers by customary methods, for example, by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

Physiologically tolerable salts of the compounds of formula I are nontoxic salts that are physiologically acceptable, in particular pharmaceutically utilizable salts. Such salts of compounds of the formula I containing acidic groups, for example carboxyl, are, for example, alkali metal salts or alkaline earth metal salts such as, for example, sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2hydroxyethyl)amine. Basic groups in the compounds of the formula I can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds of the formula I which simultaneously contain a basic group and an acidic group, for example a carboxyl group in addition to basic nitrogen atoms, can be present as zwitterions (or betaines or inner salts) which are likewise included by the present invention.

Salts of compounds of the formula I can be obtained by customary methods known to those skilled in the art, for example by combining a compound of the formula I with an inorganic or organic acid or base in a solvent or diluent, or from other salts by cation exchange or anion exchange. A subject of the present invention are also all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The present invention moreover includes all solvates of compounds of the formula I, for example hydrates or adducts with alcohols, and also derivatives of the compounds of the formula I like esters, prodrugs and other physiologically tolerable derivatives, as well as active metabolites of the compounds of the formula I. The invention relates in particular to prodrugs of the compounds of the formula I which can be converted into compounds of the formula I under physiological conditions. Suitable prodrugs for the compounds of the formula I, i. e. chemically modified derivatives of the compounds of the formula I having properties which are improved in a desired manner, are known to those skilled in the art. More detailed information relating to prodrugs and their preparation is found, for example, in Fleisher et al., Advanced Drug Delivery Reviews 19 (1996)115; Design of Prodrugs, H. Bundgaard (ed.), Elsevier, 1985; or H. Bundgaard, Drugs of the Future 16 (1991) 443; which are all incorporated herein by reference. Suitable prodrugs for the compounds of the formula I are especially ester prodrugs and amide prodrugs of carboxylic acid groups, in particular of a COOH group representing $R^2$, for example alkyl esters, and also acyl prodrugs and carbamate prodrugs of acylatable nitrogen-containing groups such as amino groups or the tetrahydronaphthyridine group. In the acyl prodrugs or carbamate prodrugs, one or more, for example one or two, hydrogen atoms on nitrogen atoms in such groups are replaced by an acyl group or a carbamate group. Suitable acyl groups and carbamate groups for the acyl prodrugs and carbamate prodrugs are, for example, the groups $R^{10}$—C(O)— and $R^{11}$O—C(O)—, in which $R^{10}$ is hydrogen, $(C_1-C_{18})$-alkyl, $(C_3-C_{14})$-cycloalkyl, $(C_3-C_4)$-cycloalkyl-$(C_1-C_8)$-alkyl-, $(C_5-C_{14})$-aryl in which 1 to 5 carbon atoms can be replaced by heteroatoms such as nitrogen, oxygen or sulfur, or $(C_5-C_{14})$-aryl-$(C_1-C_8)$-alkyl- in which 1 to 5 carbon atoms in the aryl moiety can be replaced by heteroatoms such as nitrogen, oxygen or sulfur, and in which $R^{11}$ has the meanings indicated for $R^{10}$ with the exception of hydrogen.

The present invention is furthermore not restricted to the compounds shown in formula I which contain an actual purine substructure but also includes those analogous compounds which instead of the purine substructure shown in formula I contain a 3-deazapurine substructure, 7-deazapurine substructure or 7-deaza-8-azapurine substructure, i. e. those compounds which instead of the actual purine ring system contain one of the ring systems of formula IIa, formula IIb or formula IIc wherein the 6-membered ring in the compounds of the formula I which contains the groups G and Z and to which the group E-D- is attached is symbolized by the circular arc attached to the group Z and wherein the group $R^1SO_2$—NH—CH($R^2$)—$CH_2$— is abbreviated as -EAS. All the above and following explanations relating to

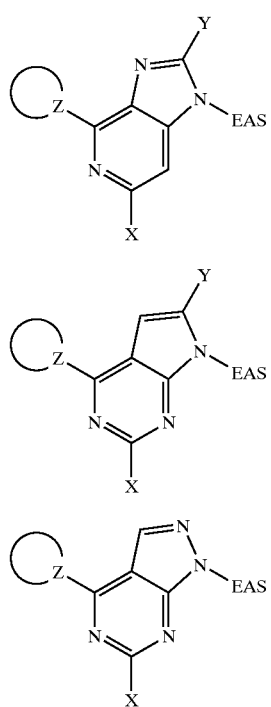

compounds of the formula I correspondingly apply to these compounds. Unless stated otherwise, if compounds of the formula I are being discussed then the deaza analogs and deaza-aza analogs are also included. Preferably, in the compounds of the invention the actual purine structure shown in formula I is present in which the nitrogen atoms in the 3-position and in the 7-position are actually present and a carbon atom to which the group Y is bonded is actually present in the 8-position.

The 6-membered ring in the compounds of formula I which can carry substituents B, can be unsubstituted or substituted where in substituted rings the substituents B can be present in any desired position. If the ring is unsubstituted this means that the number s indicating the number of substituents B is zero. In such a case, i. e. If the ring is unsubstituted and the number s is zero, all possible substituent positions on that ring which are not occupied by bonds connecting it to the neighbouring groups which are depicted in formula I, carry hydrogen atoms. If the ring is substituted this means that it carries one or more groups or atoms different from hydrogen from those groups and atoms that are listed in the definition of B, and that the number s is different from zero. In such a case, i. e. if the ring is substituted and the number s is different from zero, all positions on that ring which are not occupied by substituents B or by bonds connecting it to the adjacent groups depicted in formula I carry hydrogen atoms. The number s preferably is zero, one or two, more preferably zero, i. e. in a more preferred embodiment of the present invention the 6-membered ring containing the groups G and Z does not carry a substituent B.

These statements relating to substituents B correspondingly apply to substituents $R^3$ which can be present in the residues listed in the definition of the group E. Thus, if a residue listed in the definition of E can carry substituents $R^3$ it can be unsubstituted or substituted by $R^3$ where in substituted residues the substituents $R^3$ can be present in any desired position. If a residue is unsubstituted by $R^3$ this means that the number r indicating the number of substituents $R^3$ is zero. In such a case, i. e. if the residue is unsubstituted by $R^3$ and the number r is zero, all possible substituent positions in that residue which are not occupied by the bond symbolized by a line which connects the residue to its adjacent group D or which are not occupied by groups that are depicted in the formula, carry hydrogen atoms. If the residue is substituted this means that it carries one or more groups or atoms different from hydrogen from those groups and atoms that are listed in the definition of $R^3$, and that the number r is different from zero. In such a case, i. e. if the residue is substituted and the number r is different from zero, all positions in that residue which are not occupied by substituents $R^3$ or by other groups depicted in the formula or by the bond connecting the residue to its neighbouring group D carry hydrogen atoms. Of course, the number r in a specific residue representing E cannot exceed the number of possible substituent positions in that residue. For example, in the imidazol-2-yl residue carrying a group $R^4$ in position 1 only two substituents R can be present and r can only be 0, 1 or 2. In a 4,5-dihydroimidazol-2-yl residue or a 1,4,5, 6-tetrahydropyrimidin-2-yl residue up to four substituents can be present, for example up to four alkyl groups, and r can be 0, 1, 2, 3 or 4. In general the number r preferably is zero, one or two, more preferably zero, i. e. in a more preferred embodiment of the present invention the residues representing E do not carry any substituents $R^3$.

The number v preferably is 1 or 2, i. e. the group $(<)_v$ in the respective formulae of heterocyclic residues representing E preferably is the group —$CH_2$— or —$CH_2$—$CH_2$—.

The groups B preferably are independently of one another hydroxy or $(C_1-C_{18})$-alkyl, more preferably hydroxy or $(C_1-C_6)$-alkyl, particularly preferably hydroxy or $(C_1-C_4)$-alkyl. In case the substituents B denote aromatic or non-aromatic ring systems that are fused (or annelated) to the 6-membered ring containing the groups G and Z such ring systems are preferably fused to the sides of said 6-membered ring which do neither comprise the group G nor the group Z. If aromatic or non-aromatic ring systems are fused to the 6-membered ring containing the groups G and Z preferably one or two, more preferably one, ring systems are fused to said ring. Preferred ring systems that may be fused to the 6-membered ring containing the groups G and Z are the cyclopentane ring, the cyclohexane ring, the benzene ring, the naphthalene ring and the pyridine ring which latter ring may be fused via its carbon atoms 2 and 3 or via its carbon atoms 3 and 4, in particular the benzene ring.

The group D preferably is —C(O)—N($R^6$)—, where this divalent residue is bonded to the group E via its nitrogen atom.

The group E preferably is a residue from the series consisting of

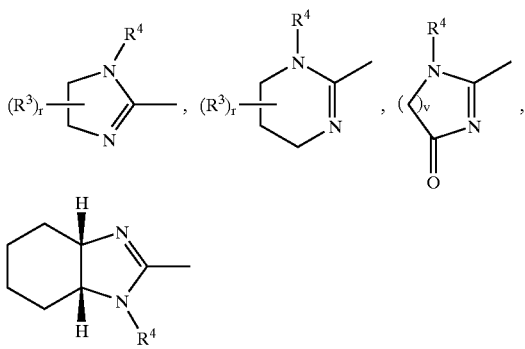

and $R^6R^{6'}$N—C(=$NR^6$)—, more preferably a residue from the series consisting of

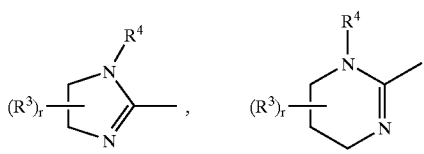

and $R^6R^{6'}$N—C(=$NR^6$)—, particularly preferably a residue from the series consisting of

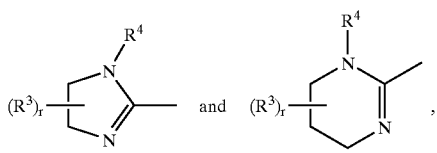

more particularly preferably the residue

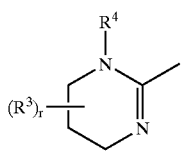

The group G preferably is N or CH, more preferably CH.

The group X preferably is hydrogen, $NR^6R^{6'}$, hydroxy-($C_1$–$C_6$)-alkyl-NH— or —NH—C(O)—$R^6$, more preferably hydrogen, $NR^6R^{6'}$ or —NH—C(O)—$R^6$, particularly preferably hydrogen or $NH_2$, more particularly preferably hydrogen.

The group Y preferably is hydrogen.

The group Z preferably is N, i. e. a nitrogen atom.

$R^1$ preferably is ($C_1$–$C_{18}$)-alkyl, ($C_3$–$C_{14}$)-cycloalkyl, ($C_3$–$C_{14}$)-cycloalkyl-($C_1$–$C_4$)-alkyl-, ($C_5$–$C_{14}$)-aryl, ($C_5$–$C_{14}$)-aryl-($C_1$–$C_4$)-alkyl-, ($C_5$–$C_{14}$)-heteroaryl or ($C_5$–$C_{14}$)-heteroaryl-($C_1$–$C_4$)-alkyl-, more preferably ($C_5$–$C_{14}$)-aryl, where aryl, heteroaryl, cycloalkyl and alkyl can be substituted one, two or three times by identical or different substituents from the series consisting of fluorine, chlorine, bromine, cyano, trifluoromethyl, ($C_1$–$C_6$)-alkyl, ($C_1$–$C_6$)-alkoxy and ($C_5$–$C_{14}$)-aryl.

$R^2$ preferably is —C(O)$R^5$. A residue of a heterocycle representing $R^2$ preferably is one of the residues tetrazolyl, imidazolyl, pyrazolyl, oxazolyl and thiadiazolyl which are bonded via ring carbon atom.

The residues $R^3$ preferably are ($C_1$–$C_6$)-alkyl, ($C_3$–$C_{14}$)-cycloalkyl, ($C_3$–$C_{14}$)-cycloalkyl-($C_1$–$C_8$)-alkyl-, fluorine, chlorine, bromine, cyano, trifluoromethyl, hydroxy or ($C_1$–$C_6$)-alkoxy, more preferably ($C_1$–$C_6$)-alkyl, fluorine, chlorine, bromine, cyano, hydroxy or ($C_1$–$C_6$)-alkoxy, where all residues $R^3$ are independent of one another and can be identical or different.

$R^4$ preferably is hydrogen or ($C_1$–$C_4$)-alkyl, more preferably hydrogen.

The residues $R^5$ and $R^{5'}$ preferably are independently of one another hydroxy or ($C_1$–$C_8$)-alkoxy, more preferably hydroxy or ($C_1$–$C_6$)-alkoxy, particularly preferably preferably hydroxy or ($C_1$–$C_6$)-alkoxy.

$R^6$ and $R^{6'}$ preferably are hydrogen, ($C_1$–$C_6$)-alkyl, ($C_3$–$C_{14}$)-cycloalkyl, ($C_3$–$C_{14}$)-cycloalkyl-($C_1$–$C_8$)-alkyl- or ($C_5$–$C_{14}$)-aryl-($C_1$–$C_8$)-alkyl-, or $R^6$ and $R^{6'}$ together with the nitrogen atom to which they are bonded form a 4-membered to 6-membered ring a system which in addition to the nitrogen atom to which $R^6$ and $R^{6'}$ are bonded can contain one or two ring heteroatoms from the series consisting of nitrogen, oxygen and sulfur and which can be unsaturated or saturated, where all residues $R^6$ and $R^{6'}$ are independent of one another and can be identical or different. More preferably $R^6$ and $R^{6'}$ are hydrogen or ($C_1$–$C_4$)-alkyl, or $R^6$ and $R^{6'}$ together with the nitrogen atom to which they are bonded form a 4-membered to 6-membered ring system which in addition to the nitrogen atom to which $R^6$ and $R^{6'}$ are bonded can contain one ring heteroatom from the series consisting of nitrogen, oxygen and sulfur and which can be unsaturated or saturated. Particularly preferably $R^6$ and $R^{6'}$ are hydrogen or ($C_1$–$C_4$)-alkyl, more particularly preferably $R^6$ is hydrogen. The residue of a ring system formed by $R^6$ and $R^{6'}$ together with the nitrogen atom to which they are bonded, preferably is derived from a saturated ring system, more preferably it is derived from one of the ring systems pyrrolidine, piperidine, morpholine, thiomorpholine and piperazine. Particularly preferably the residue $R^6R^{6'}$N— is one of the residues pyrrolidin-1-yl, piperidin-1-yl, morpholin-4-y, thiomorpholin-4-yl, piperazin-1-yl and 4-substituted piperazin-1-yl like, for example, 4-($C_1$–$C_4$)-alkyl-piperazin-1-yl.

In the compounds of formula I according to the invention the various groups, residues and numbers can independently of one another have the above preferred definitions or can have one or more of the specific denotations given in their respective definitions or in the general explanations on the respective groups and residues.

Preferred compounds of the present invention are those compounds of the formula I in which one or more of the residues have preferred definitions, or have one or more specific denotations given in their respective definitions or general explanations, all combinations of such preferred definitions and specific denotations being a subject of the present invention.

A group of preferred compounds is formed, for example, by compounds of the formula I in which B is ($C_1$–$C_{18}$)-alkyl or hydroxy, where all residues B are independent of one another and can be identical or different;

D is —C(O)—N($R^6$)—, where this divalent residue is bonded to the group E via its nitrogen atom;

E is a residue from the series consisting of

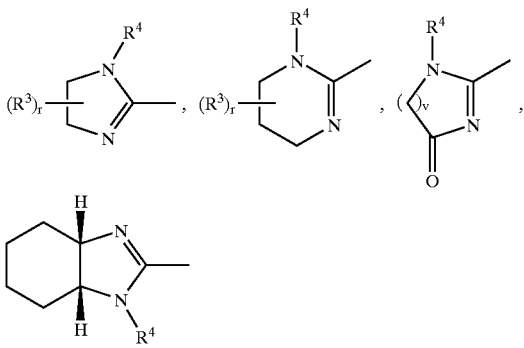

and $R^6R^{6'}N—C(=NR^6)—$;
G is N or CH;
X is hydrogen;
Y is hydrogen,
Z is N or CH;
$R^1$ is $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl or $(C_5-C_{14})$-heteroaryl-$(C_1-C_8)$-alkyl- where aryl, heteroaryl, cycloalkyl and alkyl can be substituted one, two or three times by identical or different substituents from the series consisting of fluorine, chlorine, bromine, cyano, trifluoromethyl, nitro, hydroxycarbonyl-, $(C_1-C_6)$-alkyl, $(C_1-C_6)$-alkoxy, $(C_1-C_6)$-alkoxy-$(C_1-C_6)$-alkyl-, $(C_1-C_6)$-alkoxycarbonyl-, $(C_1-C_6)$-alkylcarbonyl-, $(C_1-C_6)$-alkylaminocarbonyl-, $(C_1-C_6)$-alkoxy-$(C_1-C_6)$-alkoxy-, $(C_5-C_{14})$-arylcarbonyl-, $(C_5-C_{14})$-aryl-$(C_1-C_8)$-alkylcarbonyl-, $(C_1-C_6)$-alkanoylamino-, $(C_5-C_{14})$-arylsulfonylamino-, $(C_1-C_6)$-alkylsulfonylamino-, $(C_1-C_6)$-alkylamino-, di-$((C_1-C_6)$-alkyl)-amino-, $(C_1-C_6)$-alkylsulfonyl-, $(C_1-C_6)$-alkylaminosulfonyl-, $(C_5-C_{14})$-arylaminosulfonyl-, $(C_5-C_{14})$-aryl-$(C_1-C_8)$-alkylaminosulfonyl-, $(C_5-C_{14})$-arylsulfonyl-, $(C_5-C_{14})$-aryl-$(C_1-C_8$alkylsulfonyl-, $(C_5-C_{14})$-aryl and $(C_5-C_{14})$-heteroaryl;
$R^2$ is $—C(O)R^5$;
$R^3$ is $(C_1-C_6)$-alkyl, $(C_3-C_{14}$-cycloalkyl, $(C_3-C_{14})$-cycloalkyl-$(C_1-C_8)$-alkyl-, fluorine, chlorine, bromine, cyano, trifluoromethyl, hydroxy or $(C_1-C_6)$-alkoxy, where all residues $R^3$ are independent of one another and can be identical or different;
$R^4$ is hydrogen or $(C_1-C_6)$-alkyl;
$R^5$ is hydroxy or $(C_1-C_8)$-alkoxy;
$R^6$ and $R^{6'}$ are hydrogen, $(C_1-C_6)$-alkyl, $(C_3-C_{14})$-cycloalkyl, $(C_3-C_{14})$-cycloalkyl-$(C_1-C_8)$-alkyl-, $(C_5-C_{14})$-aryl where in the aryl residue one, two or three ring carbon atoms can be replaced by heteroatoms from the series consisting of nitrogen, oxygen and sulfur, or $(C_5-C_{14})$-aryl-$(C_1-C_8)$-alkyl- where in the aryl moiety of the aryl-alkyl-residue one, two or three ring carbon atoms can be replaced by heteroatoms from the series consisting of nitrogen, oxygen and sulfur, or $R^6$ and $R^{6'}$ together with the nitrogen atom to which they are bonded form a 4-membered to 6-membered ring system which in addition to the nitrogen atom to which $R^6$ and $R^{6'}$ are bonded can contain one, two or three ring heteroatoms from the series consisting of nitrogen, oxygen and sulfur and which can be unsaturated or saturated, where all residues $R^6$ and $R^{6'}$ are independent of one another and can be identical or different;
r is zero, one, two, three or four;
s is zero, one, two, three or four;
v is one, two or three;
in all their stereoisomeric forms and mixtures thereof in all ratios, and their physiologically tolerable salts and their prodrugs;
where in this group of compounds the analogs of the compounds of formula I having a 3-deazapurine structure, a 7-deazapurine structure or a 7-deaza-8-azapurine structure are not included.

A group of more preferred compounds is formed, for example, by compounds of the formula I in which
B is $(C_1-C_6)$-alkyl or hydroxy, where all residues B are independent of one another and can be identical or different;
D is $—C(O)—N(R^6)—$, where this divalent residue is bonded to the group E via its nitrogen atom;
E is a residue from the series consisting of

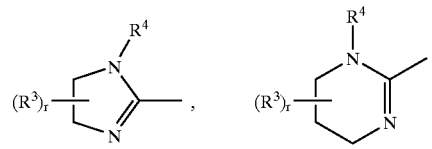

and $R^6R^{6'}N—C(=NR^6)—$;
G is N or CH;
X is hydrogen;
Y is hydrogen;
Z is N;
$R^1$ is $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-8)$-alkyl-, $(C_5-C_{14})$-heteroaryl or $(C_1-C_{14})$-heteroaryl-$(C_1-C_8)$-alkyl- where aryl, heteroaryl, cycloalkyl and alkyl can be substituted one, two or three times by identical of different substituents from the series consisting of fluorine, chlorine, bromine, cyano, trifluoromethyl, nitro, hydroxycarbonyl-, $(C_1-C_6)$-alkyl, $(C_1-C_6)$-alkoxy, $(C_1-C_6)$-alkoxy-$(C_1-C_6)$-alkyl-, $(C_1-C_6)$-alkoxycarbonyl-, $(C_1-C_6)$-alkylcarbonyl, $(C_1-C_6)$-alkylaminocarbonyl-, $(C_1-C_6)$-alkoxy-$(C_1-C_6)$-alkoxy-, $(C_5-C_{14})$-arylcarbonyl-, $(C_5-C_{14})$-aryl-$(C_1-C_8)$-alkylcarbonyl-, $(C_1-C_6)$-alkanoylamino-, $(C_5-C_{14})$-arylsulfonylamino-, $(C_1-C_6)$-alkylsulfonylamino-, $(C_1-C_6)$-alkylamino-, di-$((C_1-C_6)$-alkyl)-amino-, $(C_1-C_6)$-alkylsulfonyl-, $(C_1-C_6)$-alkylaminosulfonyl-, $(C_5-C_{14})$-arylaminosulfonyl-, $(C_5-C_{14})$-aryl-$(C_1-C_8)$-alkylaminosulfonyl-, $(C_5-C_{14})$-arylsulfonyl-, $(C_5-C_{14})$-aryl-$(C_1-C_8)$-alkylsulfonyl-, $(C_5-C_{14})$-aryl and $(C_5-C_{14})$-heteroaryl;
$R^2$ is $—C(O)R^5$;
$R^3$ is $(C_1-C_6)$-alkyl, fluorine, chlorine, bromine, cyano, hydroxy or $(C_1-C_6)$-alkoxy, where all residues $R^3$ are independent of one another and can be identical or different;
$R^4$ is hydrogen or $(C_1-C_4)$-alkyl;
$R^5$ is hydroxy or $(C_1-C_6)$-alkoxy;
$R^6$ and $R^{6'}$ are hydrogen, $(C_1-C_6)$-alkyl, $(C_3-C_{14})$-cycloalkyl, $(C_3-C_{14})$-cycloalkyl-$(C_1-C_8)$-alkyl- or $(C_5-C_{14})$-aryl-$(C_1-C_8)$-alkyl-, or $R^6$ and $R^{6'}$ together with the nitrogen atom to which they are bonded form a 4-membered to 6-membered ring system which in addition to the nitrogen atom to which $R^6$ and $R^{6'}$ are bonded can contain one or two ring heteroatoms from the series consisting of nitrogen, oxygen and sulfur and which can be unsaturated or saturated, where all residues $R^6$ and $R^{6'}$ are independent of one another and can be identical or different;

r is zero, one, two, three or four;

s is zero, one or two;

in all their stereoisomeric forms and mixtures thereof in all ratios, and their physiologically tolerable salts and their prodrugs;

in where in this group of compounds the analogs of the compounds of formula I having a 3-deazapurine structure, a 7-deazapurine structure or a 7-deaza-8-azapurine structure are not included.

A group of particularly preferred compounds is formed, for example, by compounds of the formula I in which D is —C(O)—N($R^6$)—, where this divalent residue is bonded to the group E via its nitrogen atom;

E is a residue from the series consisting of

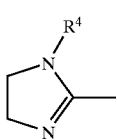 and 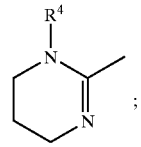 ;

G is CH;

X is hydrogen;

Y is hydrogen;

Z is N;

$R^1$ is $(C_1–C_{18})$-alkyl, $(C_3–C_{14})$-cycloalkyl, $(C_3–C_{14})$-cycloalkyl-$(C_1–C_8)$-alkyl-, $(C_5–C_{14})$-aryl, $(C_5–C_{14})$-aryl-$(C_1–C_8)$-alkyl-, $(C_5–C_{14})$-heteroaryl or $(C_5–C_{14})$-heteroaryl-$(C_1–C_8)$-alkyl- where aryl, heteroaryl, cycloalkyl and alkyl can be substituted one, two or three times by identical of different substituents from the series consisting of fluorine, chlorine, bromine, cyano, trifluoromethyl, nitro, hydroxycarbonyl-, $(C_1–C_6)$-alkyl, $(C_1–C_6)$-alkoxy, $(C_1–C_6)$-alkoxy-$(C_1–C_6)$-alkyl-, $(C_1–C_6)$-alkoxycarbonyl-, $(C_1–C_6)$-alkylcarbonyl-, $(C_1–C_6)$-alkylaminocarbonyl-, $(C_1–C_6)$-alkoxy-$(C_1–C_6)$-alkoxy-, $(C_5–C_{14})$-arylcarbonyl-, $(C_5–C_{14})$-aryl-$(C_1–C_6)$-alkylcarbonyl-, $(C_1–C_6)$-alkanoylamino-, $(C_5–C_{14})$-arylsulfonylamino-, $(C_1–C_6)$-alkylsulfonylamino-, $(C_1–C_6)$-alkylamino-, di-$((C_1–C_6)$-alkyl)-amino-, $(C_1–C_6)$-alkylsulfonyl-, $(C_1–C_6)$-alkylaminosulfonyl-, $(C_5–C_{14})$-arylaminosulfonyl-, $(C_5–C_{14})$-aryl-$(C_1–C_8)$-alkylaminosulfonyl-, $(C_5–C_{14})$-arylsulfonyl-, $(C_5–C_{14})$-aryl-$(C_1–C_8)$-alkylsulfonyl-, $(C_5–C_{14})$-aryl and $(C_5–C_{14})$-heteroaryl;

$R^2$ is —C(O)$R^5$;

$R^4$ is hydrogen or $(C_1–C_4)$-alkyl;

$R^5$ is hydroxy or $(C_1–C_6)$-alkoxy;

$R^6$ is hydrogen or $(C_1–C_4)$-alkyl;

s is zero;

in all their stereoisomeric forms and mixtures thereof in all ratios, and their physiologically tolerable salts and their prodrugs;

where in this group of compounds the analogs of the compounds of formula I having a 3-deazapurine structure, a 7-deazapurine structure or a 7-deaza-8-azapurine structure are not included. In this group of compounds the number r of substituents in the residue E is zero.

A group of more particularly preferred compounds is formed, for example, by compounds of the formula I in which D is —C(O)—NH—, where this divalent residue is bonded to the group E via its nitrogen atom;

E is the residue

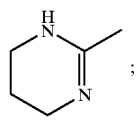 ;

G is CH;

X is hydrogen;

Y is hydrogen;

Z is N;

$R^1$ is $(C_1–C_8)$-alkyl, $(C_3–C_{14})$-cycloalkyl, $(C_3–C_{14})$-cycloalkyl-$(C_1–C_6)$-alkyl-, $(C_5–C_{14})$-aryl, $(C_5–C_{14})$-aryl-$(C_1–C_8)$-alkyl-, $(C_5–C_{14})$-heteroaryl or $(C_5–C_{14})$-heteroaryl-$(C_1–C_8)$-alkyl- where aryl, heteroaryl, cycloalkyl and alkyl can be substituted one, two or three times by identical or different substituents from the series consisting of fluorine, chlorine, bromine, cyano, trifluoromethyl, $(C_1–C_6)$-alkyl, $(C_1–C_6)$-alkoxy and $(C_5–C_{14})$-aryl;

$R^2$ is —C(O)$R^5$;

$R^5$ is hydroxy or $(C_1–C_6)$-alkoxy;

s is zero;

in all their stereoisomeric forms and mixtures thereof in all ratios, and their physiologically tolerable salts and their prodrugs;

where in this group of compounds the analogs of the compounds of formula I having a 3-deazapurine structure, a 7-deazapurine structure or a 7-deaza-8-azapurine structure are not included. In this group of compounds the number r of substituents in the residue E is zero. This group of compounds can also be represented by the formula Ia

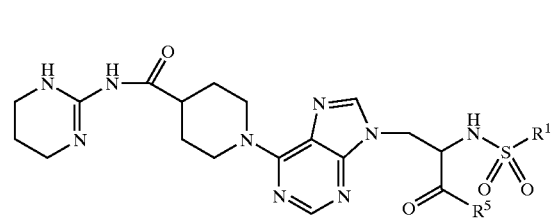

Ia wherein $R^1$ and $R^5$ have the before-mentioned meanings.

Further, preferred compounds of the present invention are those compounds in which the asymmetric carbon atom in the formula I to which the groups $R^2$ and $R^1$—SO$_2$—NH— are bonded, has S configuration, and their physiologically tolerable salts and their prodrugs.

The present invention also relates to processes of preparation by which the compounds of the formula I are obtainable and which comprise carrying out one or more of the synthesis steps described below. The compounds of the formula I can generally be prepared, for example in the course of a convergent synthesis, by linkage of two or more fragments which can be derived retrosynthetically from the formula I. In the preparation of the compounds of the formula I it can generally be advantageous or necessary in the course of the synthesis to introduce functional groups which could lead to undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991). As examples of precursor groups nitro groups and cyano groups may be mentioned which can later be converted by reduction, for example by catalytic hydrogenation, into amino groups and aminomethyl groups, respectively. The protective groups exemplarily mentioned above with respect to functional groups in amino acid residues present in the compounds of formula I correspondingly can be used as protective groups for functional groups during the synthesis of the compounds of formula I.

For example, for the preparation of a compound of the formula I a building block of the formula III

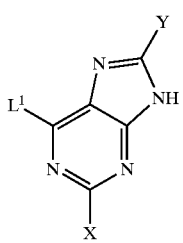

III in which $L^1$ is a customary nucleophilically substitutable leaving group, can be used. Suitable groups $L^1$ are known to those skilled in the art and can be, for example chlorine, bromine, iodine, or a sulfonyloxy group like p-toluenesulfonyloxy (-OTos), methanesulfonyloxy (-OMes) or trifluoromethanesulfonyloxy (-OTf), preferably chlorine or bromine. X and Y in the compounds of formula III are as defined above but functional groups can optionally also be present in the form of precursor groups or can be protected by protective groups. The compound of the formula III is reacted with a building block of the formula IV $L^2$—$CH_2$—$CH(R^2)$—$NHR^{15}$

wherein $R^2$ is as defined above but where functional groups in $R^2$ can optionally also be present in the form of precursor groups or can be protected by protective groups. In particular, for example, a group $R^2$ in a compound of the formula I denoting hydroxycarbonyl-(—COOH) is preferably present in a starting compound of the formula IV as an ester like a tert-butyl ester or a methyl ester or an ethyl ester group. The group $L^2$ in the compounds of formula IV is hydroxy or a customary nucleophilically substitutable leaving group. Suitable leaving groups $L^2$ are known to those skilled in the art and can be, for example chlorine, bromine, iodine, -OTos, -OMes or -OTf. The group $R^{15}$ stands for the group $R^1$—$SO_2$— wherein $R^1$ is as defined above, or $R^{15}$ is an amino protecting group. Suitable amino protecting groups are known to those skilled in the art (see, for example, Greene and Wuts, Protective Groups in Organic Synthesis, Wiley, 1991). Examples of amino protecting groups are the benzyloxycarbonyl group, the tert-butoxycarbonyl group or the 9-fluorenylmethoxycarbonyl group. From the compounds of formulae III and IV a compound of formula V

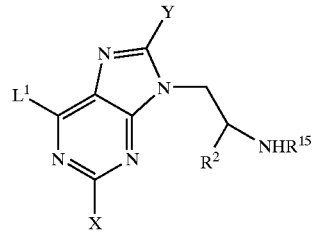

V is obtained wherein $L^1$, X, Y, $R^2$ and $R^{15}$ are as defined above but wherein functional groups can optionally also be present in the form of precursor groups or can be protected by protective groups. The reaction of the compounds of formula III and IV can be carried out according to methods known to those skilled in the art (see, for example, J. March, Advanced Organic Chemistry, Fourth Edition, Wiley, 1992, and source literature quoted therein). Preferably, the reaction is carried out in a suitable organic solvent or diluent, for example dichloromethane (DCM), chloroform, tetrahydrofuran (THF), diethyl ether, n-heptane, n-hexane, n-pentane, cyclohexane, diisopropyl ether, methyl tert-butyl ether, acetonitrile, dimethylformamide (DMF), dimethylsulfoxide (DMSO), dioxane, toluene, benzene, ethyl acetate or a mixture of these solvents, if appropriate with addition of a base such as, for example, butyllithium, lithium diisopropylamide (LDA), sodium hydride, sodium amide, potassium tert-butoxide, calcium carbonate, cesium carbonate, triethylamine, N,N-diisopropylethylamine or a complex base (for example sodium amide together with an alcoholate $R^{25}ONa$, where $R^{25}$ is $(C_2-C_6)$-alkyl or $CH_3CH_2OCH_2CH_2$—). With compounds of the formula IV in which $L^2$ is hydroxy the reaction is carded out after activation of the hydroxy group, for example by reaction with triphenylphosphine and diethyl azodicarboxylate (DEAD) in THF under the conditions of the well-known Mitsunobu reaction.

For the preparation of a compound of the formula I in which Z is nitrogen a compound of the formula V is then reacted with a compound of the formula VIa

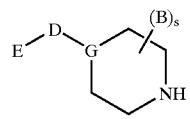

VIa wherein B, D, E, G and s are defined as above but wherein functional groups can optionally also be present in the form of precursor groups or can be protected by protective groups. The reaction of the compounds of the formulae V and VIa can be carried out according to methods well-known to those skilled in the art (see, for example, J. March, Advanced Organic Chemistry, Fourth Edition, Wiley, 1992, and source literature quoted therein). In the reaction of a compound of the formula V with a compound of the formula Via a nucleophilically substitutable leaving group in one reaction partner is replaced with a nucleophilic nitrogen atom in the other reaction partner as in the case of the reaction of the compounds of formulae III and IV. The above explanations on solvents or bases suitable for the reaction of the compounds of formulae III and IV therefore correspondingly apply to the reaction of the compounds of formulae V and VIa. As a base in the reaction of the compounds of the formulae V and VIa also an excess of the compound of the formula VIa can be used.

For the preparation of a compound of the formula I in which Z is CH a compound of the formula V is reacted with a compound of the formula VIb

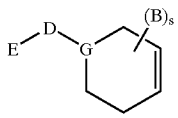

VIb wherein B, D, E, G and s are defined as above but wherein functional groups can optionally also be present in the form of precursor groups or can be protected by protective groups. The reaction of the compounds of the formulae V and VIb can be carried out under the conditions of the Stille coupling as described, for example, in Langli et al., Tetrahedron 52 (1996) 5625 or Gundersen, Tetrahedron Lett. 35 (1994) 3153, or under the conditions of the Heck coupling as described, for example, in Koyama et al., Nucleic Adds Res., Symp. Ser. 11 (1982) 41 which are all incorporated herein by reference.

The reaction of a compound of the formula V with a compound of the formula VIa or VIb, respectively, leads to a compound of the formula VII,

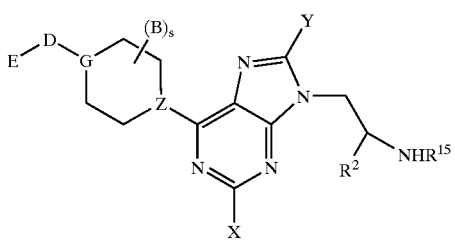

VII wherein B, D, E, G, X, Y, Z, $R^2$, $R^{15}$ and s are defined as above but wherein functional groups can optionally also be present in the form of precursor groups or can be protected by protective groups. By standard processes precursor groups optionally still present in the compounds of the formula VII are then converted into the desired final groups and/or protective groups optionally still present are then removed. For example, tert-butyl ester groups, especially a tert-butyl ester group which represents the group $R^2$ in the compound of formula VII and which is a protected form of hydroxycarbonyl group representing $R^2$ in the target compound of formula I, can be converted into the carboxylic acid group by treatment with trifluoroacetic acid.

If the group $R^{15}$ in the compound of the formula VII does not stand for a group $R^1$—$SO_2$— that is to be present in the desired target molecule of the formula I but stands for an amino protecting group, a deprotection step is carried out by which the compound of the formula VII in converted into the compound of the formula VIII

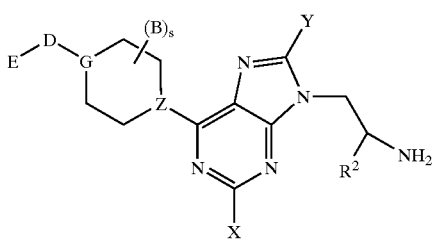

VIII wherein B, D, E, G, X, Y, Z, $R^2$ and a are defined as above but wherein functional groups can optionally also be present in the form of precursor groups or can be protected by protective groups. If, for example, $R^{15}$ is a benzyloxycarbonyl group the conversion of the group $R^{15}$NH into the group $H_2$N can be accomplished by catalytic hydrogenation, for example over palladium on charcoal in a solvent like acetic acid or ethanol or methanol, if $R^{15}$ is a 9-fluorenylmethoxycarbonyl group the conversion of the group $R^{15}$NH into the group $H_2$N can be accomplished by treatment with piperidine.

For the introduction of the group $R^1$—$SO_2$— the compound of the formula VIII is then reacted with a sulfonic acid halide of the formula $R^1$—$SO_2$—Hal or a sulfonic acid anhydride of the formula $R^1$—$SO_2$—O—$SO_2$—$R^1$ wherein $R^1$ is as defined above and Hal denotes fluorine, chlorine or bromine, preferably chlorine. This sulfonylation reaction is preferably carried out in a suitable organic solvent or diluent, for example in dimethylformamide, N-methylpyrrolidone, dichloromethane, chloroform, tetrahydrofuran, dioxane, dimethylsulfoxide, toluene, benzene, ethyl acetate or a mixture of these solvents, optionally with addition of a base such as, for example, triethylamine or N,N-diisopropylethylamine.

In the synthesis of a compound of the formula I it is also possible first to react a compound of the formula III with a compound of the formula VIa or VIb leading to replacement of the group $L^1$ in the formula III by the 6-membered ring, and subsequently to react the resulting intermediate with a compound of the formula IV.

If desired, with the compounds of the formula VII or with the sulfonylation products of the compounds of the formula VII further reactions can then be carried out by standard processes, for example acylation reactions or esterification reactions. Further, for example, a substituent X in the 2-position of the purine structure can also be introduced only at the end of the above-described synthesis of the compounds of formula I by methods known per se, for example as described in D. A Nugiel, J. Org. Chem. 62 (1997) 201 or N. S. Gray, Tetrahedron Lett. 38 (1997)1161 and the references quoted therein, and a substituent Y in the 8-position can be introduced by methods known per se as described, for example, in E. J. Reist et al., J. Org. Chem. 33 (1968) 1600; J. L. Kelley et al., J. Med. Chem. 33 (1990) 196 or E. Vanotti et al., Eur. J. Chem. 29 (1994) 287 which are all incorporated herein by reference. In addition, if desired a compound of the formula VII or a sulfonylation product of a compound of the formula VII can be converted into a physiologically tolerable salt or a prodrug by standard processes known to those skilled in the art.

Compounds of the formula I in which D is —CO—$NR^6$— wherein the nitrogen atom is bonded to the group E, the group G is CH and the group Z is nitrogen can also be prepared via the following route. A compound of the formula V is reacted with an compound of the formula IX to give a compound of the formula X.

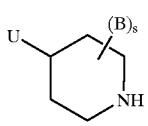

IX

-continued

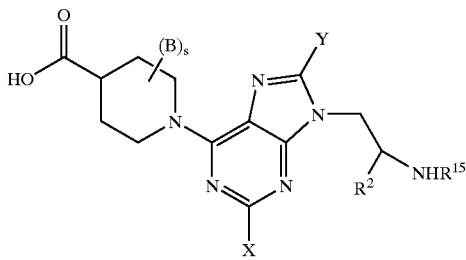

B, X, Y, $R^2$, $R^{15}$ and s in the compounds of formulae IX and X are as defined above but functional groups can optionally also be present in the form of precursor groups or can be protected by protective groups. The group U in the compounds of formula IX is a carboxylic add group COOH or a suitably protected carboxylic acid group, for example a benzyl ester, tert-butyl ester or sill ester. If U is a protected carboxylic acid group preferably the protective group is chosen such that it can be deprotected independently from other protected carboxylic acid groups that may be present, for example in $R^2$, or from a protecting group $R^7$. The reaction of the compounds of the formulae IX and X can be carried out according to methods well known to those skilled in the art (see, for example, J. March, Advanced Organic Chemistry, Fourth Edition, Wiley, 1992, and source literature quoted therein). In the reaction of a compound of the formula IX with a compound of the formula X a nucleophilically substitutable leaving group in one reaction partner is replaced with a nucleophilic nitrogen atom in the other reaction partner as, for example, in the case of the reaction of the compounds of formulae III and IV. The above explanations on solvents or bases suitable for the reaction of the compounds of formulae III and IV therefore correspondingly apply to the reaction of the compounds of formulae IX and X. As a base in the reaction of the compounds of the formulae IX and X also an excess of the compound of the formula IX can be used. If a compound of the formula IX is used in which U is the group COOH the reaction directly leads to a compound of the formula X. Otherwise the compound of the formula X is obtained after removal of the carboxylic add protecting group present in U according to known methods.

The carboxylic acid group in the 4-position of the piperidin-1-yl residue in the compounds of the formula I can then be activated, for example by methods used for peptide couplings which are well known to those skilled in the art and which are reviewed, for example, in F. Albericio and L. A. Carpino, Methods Enzymol. 289 (1997), 104. Examples of suitable activating agents are O-((cyano-(ethoxycarbonyl)-methylen)-amino)1,1,3,3-tetramethyluronium tetrafluoroborate (TOTU), O-benzotriazol-1-yl-N,N,N',N'-tetramethyluronium hexafluorophosphate (HBTU), O-(7-azabenzotriazol-1-yl)-N,N,N',N'-tetramethyluronium hexafluorophosphate (HBTU), or carbodiimides like N,N'-dicyclohexylcarbodiimide or N,N'-diisopropylcarbodiimide. Activation can also favorably be accomplished by converting the carboxylic acid into the pentafluorophenyl ester by reaction with N,N'-dicyclohexylcarbodiimide and pentafluorophenol. After activation the compound of the formula X is reacted with a compound of the formula H—$NR^6$—E in which $R^6$ and E are as defined above but functional groups can optionally also be present in the form of precursor groups or can be protected by protective groups, to give a compound of the formula VII in which D stands for C(O)—$NR^6$ wherein the nitrogen atom is bonded to the group E, the group G stands for CH and the group Z stands for nitrogen. The compound of the formula VII is then converted into the formula I as outlined above.

The starting compounds of the formulae III, IV, VIa, VIb and IX which are linked to give the compounds of the formula I, are commercially available or can be prepared by or analogously to processes described below or in the literature.

The compounds of the formula I are valuable pharmacologically active compounds which are suitable, for example, for the therapy and prophylaxis of bone disorders, tumor diseases, cardiovascular disorders or inflammatory conditions. The compounds of the formula I and their physiologically tolerable salts and their prodrugs can be administered to animals, preferably to mammals, and in particular to humans as pharmaceuticals for therapy or prophylaxis. They can be administered on their own or in mixtures with one another or in the form of pharmaceutical compositions which permit enteral or parenteral administration and which, as active constituent, contain an efficacious dose of at least one compound of the formula I and/or its physiologically tolerable salts and/or its prodrugs in addition to customary pharmaceutically acceptable carder substances and/or additives.

The present invention therefore also relates to the compounds of the formula I and/or their physiologically tolerable salts and/or their prodrugs for use as pharmaceuticals, to the use of the compounds of the formula I and/or their physiologically tolerable salts and/or their prodrugs for the production of pharmaceuticals for the therapy and prophylaxis of the diseases mentioned above or below, for example for the therapy and prophylaxis of bone disorders, and also to the use of the compounds of the formula I and/or their physiologically tolerable salts and/or their prodrugs for the therapy and prophylaxis of these diseases and to methods for such therapy and prophylaxis. The present invention furthermore relates to pharmaceutical compositions (or pharmaceutical preparations) which contain an efficacious dose of at least one compound of the formula I and/or its physiologically tolerable salts and/or its prodrugs and a customary pharmaceutically acceptable carrier.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions emulsions or tinctures, or in other ways, for example in the form of aerosols or nasal sprays.

The pharmaceutical compositions according to the invention are prepared in a manner known per se and familiar to those skilled in the art, one or more compound(s) of the formula I and/or its (their) physiologically tolerable salts and/or its (their) prodrugs being mixed with one or more pharmaceutically acceptable inert inorganic and/or organic carrier substances and/or additives and, if desired, one or more other pharmaceutically active compounds and being brought into a suitable administration form and dosage form that can be used in human or veterinary medicine. For the production of pills, tablets, coated tablets and hard gelatin capsules it is possible to use, for example, lactose, corn starch or derivatives thereof, talc, stearic acid or its salts, etc.

Carriers for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical compositions normally contain about 0.5 to 90% by weight of the compounds of the formula I and/or their physiologically tolerable salts and/or their prodrugs. The amount of the active ingredient of the formula I and/or its physiologically tolerable salts and/or its prodrugs in the pharmaceutical compositions normally is from about 0.2 mg to about 500 mg, preferably from about 1 mg to about 200 mg.

In addition to the active ingredients of the formula I and/or its physiologically tolerable salts and/or its prodrugs and carriers, the pharmaceutical compositions can contain additives (or auxiliary substances) such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I and/or their physiologically tolerable salts and/or their prodrugs. Furthermore, in addition to at least one compound of the formula I and/or its physiologically tolerable salts and/or its prodrugs, they can also contain one or more other therapeutically or prophylactically active ingredients.

The compounds of the formula I are antagonists of the vitronectin receptor and inhibitors of cell adhesion. They have, for example, the ability to inhibit the binding of osteoclasts to the bone surface and thereby inhibit bone resorption by osteoclasts. The action of the compounds of the formula I can be demonstrated, for example, in an assay in which the inhibition of the binding of the isolated vitronectin receptor or of cells which contain the vitronectin receptor to a ligand of the vitronectin receptor is determined. Details of such an assay are given below. As vitronectin receptor antagonists, the compounds of the formula I and their physiologically tolerable salts and their prodrugs are generally suitable for the therapy and prophylaxis of diseases which are based on the interaction between vitronectin receptors and their ligands in cell-cell interaction processes or cell-matrix interaction processes, or which can be influenced by an inhibition of interactions of this type, or for the prevention, alleviation or cure of which an inhibition of interactions of this type is desired. As explained at the beginning, such interactions play a part, for example, in bone resorption, in angiogenesis or in the proliferation of cells of the vascular smooth musculature. The compounds of the formula I and their physiologically tolerable salts and their prodrugs are therefore suitable, for example, for the prevention, alleviation or cure of diseases which are caused at least partially by an undesired extent of bone resorption, angiogenesis or proliferation of cells of the vascular smooth musculature.

Bone diseases for whose treatment and prevention the compounds of the formula I according to the invention can be employed are especially osteoporosis, hypercalcemia, osteopenia, for example caused by metastases, dental disorders, hyperparathyroidism, periarticular erosions in rheumatoid arthritis and Paget's disease. In addition, the compounds of the formula I can be used for the alleviation, avoidance or therapy of bone disorders which are caused by a glucocorticoid, steroid or corticosteroid therapy or by a lack of sex hormone(s). All these disorders are characterized by bone loss which is based on the inequilibrium between bone formation and bone destruction and which can be favorably influenced by the inhibition of bone resorption by osteoclasts. The compounds of the formula I and/or their physiologically tolerable salts and/or their prodrugs can also favorably be used as inhibitor of bone resorption, for example in the therapy or prophylaxis of osteoporosis, in combination with conventional osteoporosis treatments, for example in combination with agents like bisphosphonates, estrogens, estrogen/progesterone, estrogen agonists/antagonists, calcitonin, vitamin D analogues, parathyroid hormone, growth hormone secretagogues, or sodium fluoride. Administration of the compounds of the formula I and/or their physiologically tolerable salts and/or their prodrugs and of other active ingredients effective in the treatment or prophylaxis of osteoporosis like those listed before can take place simultaneously or sequentially, in any order, and jointly or separately. For use in such a combination treatment or prophylaxis the compounds of the formula I and/or their physiologically tolerable salts and/or their prodrugs and one or more other active ingredients like those listed before can together be present in a single pharmaceutical composition, for example tablets, capsules or granules, or can be present in two or more separate pharmaceutical compositions which can be contained in a single package or in two or more separate packages. The use of the compounds of the formula I and/or their physiologically tolerable salts and/or their prodrugs in such a combination therapy or prophylaxis and their use in the production of pharmaceuticals for such a combination therapy or prophylaxis are also subjects of the present invention. The invention furthermore relates to pharmaceutical compositions which comprise efficacious amounts of at least one compound of the formula I and/or its physiologically tolerable salts and/or its prodrugs together with at least one other active ingredient effective in the treatment or prophylaxis of osteoporosis or in the inhibition of bone resorption like those listed before, together with a customary pharmaceutically acceptable carrier. The above explanations on pharmaceutical compositions correspondingly apply to such pharmaceutical combination compositions.

Apart from use as inhibitors of bone resorption by osteoclasts, the compounds of the formula I and their physiologically tolerable salts and their prodrugs can be used, for example, as inhibitors of tumor growth and tumor metastasis, as antiinflammatories, for the therapy or prophylaxis of rheumatoid arthritis, for the therapy of psoriasis, for the therapy or prophylaxis of cardiovascular disorders such as arteriosclerosis or restenoses, for the therapy or prophylaxis of nephropathies or retinopathies such as, for example, diabetic retinopathy. As inhibitors of tumor growth or tumor metastasis the compounds of the formula I and/or their physiologically tolerable salts and/or their prodrugs can also favorably be used in combination with conventional cancer therapy. Examples of conventional cancer therapy are given in Bertino (Editor), Encyclopedia of Cancer, Academic Press, 1997 which is incorporated herein by reference. All the above statements relating to the use of the compounds of formula I fat in combination with conventional osteoporosis therapy like, for example, possible modes of administration and pharmaceutical combination compositions, correspondingly apply to the use of the compounds of formula I in combination with conventional cancer therapy.

When using the compounds of the formula I, the dose can vary within wide limits and, as is customary, is to be suited to the individual conditions in each individual case. It depends, for example, on the compound employed, on the nature and severity of the disease to be treated, or on whether an acute or chronic condition is treated or whether prophylaxis is carried out. In the case of oral administration, the daily dose is in general from about 0.01 to about 100 mg/kg, preferably from about 0.1 to about 50 mg/kg, in particular from about 0.1 to about 5 mg/kg, to achieve effective results in an adult weighing about 75 kg (in each case in mg per kg of body weight). Also in the case of intravenous administration the daily dose is in general from about 0.01 to about 100 mg/kg, preferably from about 0.05 to about 10 mg/kg (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Apart from use as pharmaceutical active ingredients, the compounds of the formula I can also be used as vehicles or carriers of other active ingredients in order to transport the active ingredient specifically to the site of action (=drug targeting; see, for example, Targeted Drug Delivery, R. C. Juliano, Handbook of Experimental Pharmacology, Vol. 100, Ed. Born, G. V. R. et al., Springer Verlag which is incorporated herein by reference). The active ingredients to be transported are in particular those which can be used for the treatment of the abovementioned diseases.

The compounds of the formula I and their salts can furthermore be employed for diagnostic purposes, for example in in vitro diagnoses, and as auxiliaries in biochemical investigations in which blocking of the vitronectin receptor or influencing of cell-cell or cell-matrix interactions is desired. They can furthermore be used as synthesis intermediates for the preparation of other compounds, in particular of other pharmaceutical active ingredients, which are obtainable from the compounds of the formula I, for example by introduction of substituents or modification of functional groups.

EXAMPLES

| Abbreviations | |
|---|---|
| AcOH | acetic acid |
| DCM | dichloromethane |
| DMF | N,N-dimethylformamide |
| EE | ethyl acetate |
| MeOH | methanol |
| TFA | trifluoroacetic acid |
| THF | tetrahydrofuran |

Example 1

(2S)-2-(Naphthalene-1-sulfonylamino)-3-(6-(4-(1,4,5,6-tetrahydropyrimidin-2-ylcarbamoyl)-piperidin-1-yl)-purin-9-yl)-propionic acid

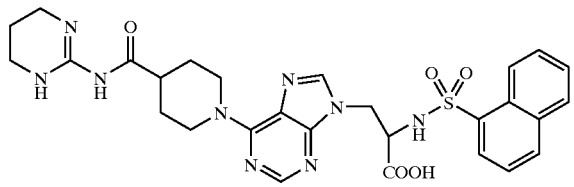

a) (2S)-2-Benzyloxycarbonylamino-3-(6-chloro-purin-9-yl)-propionic acid tert-butyl ester To a suspension of 7.73 g (50 mmol) of 6-chloropurine in 350 ml of absolute THF were added 14.43 g (55 mmol) triphenylphosphine at −10 to 0° C. followed by 9.57 g (55 mmol) of diethyl azodicarboxylate and 14.8 g (50 mmol) of N-benzyloxycarbonyl-L-serine tert-butyl ester in 100 ml of absolute THF, and the mixture was stirred at 0° C. for 48 h. The solvent was evaporated, the residue was dissolved in EE/heptane (2:1), filtered and the solvent was removed in vacuo. The crude product was purified by flash chromatography on silica gel (EE/n-heptane (1:1) and DCM/EE (85:15)). Yield: 6.6 g.

$^1$H-NMR (200 MHz, D$_6$-DMSO): δ=1.30 (s, 9H, C(CH$_3$)$_3$) 4.48–4.73 (m, 3H, CH$_2$—CH—N); 4.98 (s, 2H, CH$_2$-aryl); 7.19–7.40 (m, 5H, aryl-H); 7.87 (d, 1H, NH); 8.61+8.77 (s+s, 2H, C$^6$—H+C$^8$—H).

MS (FAB): m/e=432.1 (100%, (M+H)$^+$); 376.0 (60%).

b) 1-(9-((2S)-2-Benzyloxycarbonylamino-2-tert-butoxycarbonyl-ethyl)-purin-6-yl)-piperidine-4-carboxylic acid To 5.92 g (45.8 mmol) of piperidine-4-carboxylic acid in 200 ml of DMF were added 18.65 g (92 mmol) of N,O-bis-trimethylsilylacetamide. The mixture was brought to room temperature and stirred for 2.5 h. Then 6.6 g (15.3 mmol) of the compound of step a) in 50 ml of DMF were added and the mixture was stirred at room temperature for 18 h. The solvent was removed in vacuo and the residue dissolved in EE and extracted with aqueous KHSO$_4$/K$_2$SO$_4$ solution and saturated brine. The solution was dried over MgSO$_4$, filtered and the solvent was removed in vacuo. The crude product was purified by flash chromatography on silica gel (EE/n-heptane (1:1) and DCM/MeOH/AcOH (100:3:0.5)). Yield: 4.7 g.

MS (ES$^+$): m/e=525.4 (100%, (M+H)$^+$).

c) (2S)-2-Benzyloxycarbonylamino-3-(6-(4-(1,4,5,6-tetrahydropyrimidin-2-ylcarbamoyl)-piperidin-1-yl)-purin-9-yl)-propionic acid tert-butyl ester To 4.65 g (8.87 mmol) of the compound of step b) and 1.45 g (10.65 mmol) of 2-amino-1,4,5,6-tetrahydropyrimidine hydrochloride in 120 ml of absolute DMF were added 3.2 g (9.76 mmol) of O-((cyano-(ethoxycarbonyl)-methylen)-amino)-1,1,3,3-tetramethyluronium-tetrafluoroborate (TOTU) and 4.59 g (6.04 mmol) of N,N-diisopropylethylamine and the mixture was stirred for 5 h at room temperature. 2.66 ml of glacial acetic acid were added and the solvent was removed in vacuo. The residue was dissolved in EE and extracted with aqueous NaHCO$_3$ solution and brine, the solution was dried over MgSO$_4$, filtered and the solvent was removed in vacuo. The crude product was purified by flash chromatography on silica gel (DCM/MeOH/AcOH/H$_2$O (93:7:0.7:0.7)). Yield: 2.4 g.

MS (ES$^+$): m/e=606.5 (100%, (M+H)$^+$); 303.8 (50%); 275.8 (100%).

d) (2S)-2-Amino-3-(6-(4-(1,4,5,6-tetrahydropyrimidin-2-ylcarbamoyl)-piperidin-1-yl)-purin-9-yl)-propionic acid tert-butyl ester 1 g of the compound of step c) was dissolved in 30 ml of glacial acetic acid and hydrogenated over 0.5 g of palladium/charcoal (10%). The catalyst was filtered off, the solvent was removed in vacuo and the product was purified by flash chromatography on silica gel (DCM/MeOH/AcOH/H$_2$O (92:8:1.5:1.5)). Yield: 0.76 g.

MS (ES$^+$): m/e=472.3 (10%, (M+H)$^+$); 208.6 (100%).

e) (2S)-2-(Naphthalene-1-sulfonylamino)-3-(6-(4-(1,4,5,6-tetrahydropyrimidin-2-ylcarbamoyl)-piperidin-1-yl)-purin-9-yl)-propionic acid tert-butyl ester To 0.25 g (0.47 mmol) of the compound of step d) in 4 ml of absolute DMF were added at 0° C. 160 mg (0.7 mmol) of naphthalene-1-sulfonyl chloride and 152 mg (1.18 mmol) of N,N-diisopropylethylamine and the mixture was stirred at 0° C. for 3 hours. The solvent was removed in vacuo the residue was dissolved in EE and the solution was extracted with aqueous NaHCO$_3$ solution and brine, dried over MgSO$_4$, filtered and concentrated in vacuo. The crude product was purified by flash chromatography on silica gel (DCM/MeOH/AcOH/H$_2$O (93:7:0.7:0.7)). Yield: 183 mg.

MS (ES$^+$): m/e=662.4 (15%, (M+H)); 331.9 (30%); 303.8 (100%).

f) (2S)-2-(Naphthalene-1-sulfonylamino)-3-(6-(4-(1,4,5,6-tetrahydropyrimidin-2-ylcarbamoyl)-piperidin-1-yl)-purin-9-yl)-propionic acid 173 mg of the compound of step e) were dissolved in 40 ml of cooled 95% TFA and stirred for 30 minutes at 0° C. and then for 40 minutes at room temperature. The TFA was removed in vacuo and the product was three times co-evaporated with toluene and three times with ethanol. Yield: 190 mg (TFA salt).

MS (ES$^+$): m/e=606.3 (15%, (M+H)$^+$); 323.3 (20%); 303.8 (100%).

Example 2

(2S)-2-(Naphthalene-2-sulfonylamino)-3-(6-(4-(1,4,5,6-tetrahydropyrimidin-2-ylcarbamoyl)-piperidin-1-yl)-purin-9-yl)-propionic acid

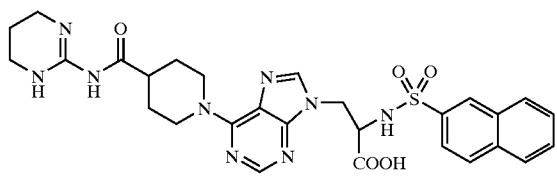

a) (2S)-2-(Naphthalene-2-sulfonylamino)-3-(6-(4-(1,4,5,6-tetrahydropyrimidin-2-ylcarbamoyl)-piperidin-1-yl)-purin-9-yl)-propionic acid tert-butyl ester The synthesis was carried out analogously to example 1e) using the compound of example 1, step d) and naphthalene-2-sulfonyl chloride. Yield: 71.3%.

MS (ES$^+$): m/e=662.4 (50%, (M+H)$^+$); 331.9 (90%); 303.8 (100%).

b) (2S)-2-(Naphthalene-2-sulfonylamino)-3-(6-(4-(1,4,5-tetrahydropyrimidin-2-ylcarbamoyl)-piperidin-1-yl)-purin-9-yl)-propionic acid The synthesis was carried out analogously to example 1f) using 80 mg of the compound of step a). Yield: 65.3 mg (TFA salt).

MS (ES$^+$): m/e=606.3 (10%, (M+H)$^+$); 324.3 (15%); 303.8 (100%).

Example 3

(2S)-2-(4-tert-Butyl-benzenesulfonylamino)-3-(6-(4-(1,4,5,6-tetrahydropyrimidin-2-ylcarbamoyl)-piperidin-1-yl)-purin-9-yl)-propionic acid

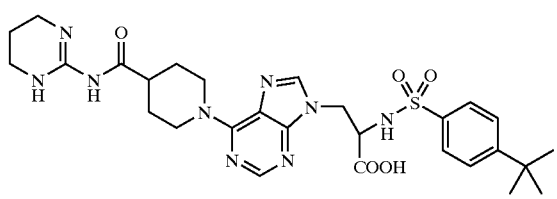

a) (2S)-2-(4-tert-Butyl-benzenesulfonylamino)-3-(6-(4-(4,5,6-tetrahydropyrimidin-2-ylcarbamoyl)-piperidin-1-yl)-purin-9-yl)-propionic acid tert-butyl ester The synthesis was carried out analogously to example 1e) using the compound of example 1, step d) and 4-tert-butyl-benzenesulfonyl chloride. Yield: 62%.

MS (ES$^+$): m/e=668.5 (30%, (M+H)$^+$); 334.8 (100%); 306.8 (80%).

b) (2S)-2-(4-tert-Butyl-benzenesulfonylamino)-3-(6-(4-(1,4,5,6-tetrahydropyrimidin-2-ylcarbamoyl)-piperidin-1-yl)-purin-9-yl)-propionic acid The synthesis was carried out analogously to example 1f) using 62 mg of the compound of step a). Yield: 48 mg (TFA salt).

MS (ES$^+$): m/e=612.4 (15%, (M+H)$^+$); 327.4 (10%); 306.8 (100%).

Example 4

(2S)-2-(Propane-1-sulfonylamino)-3-(6-(4-(1,4,5,6-tetrahydropyrimidin-2-ylcarbamoyl)-piperidin-1-yl)-purin-9-yl)-propionic acid

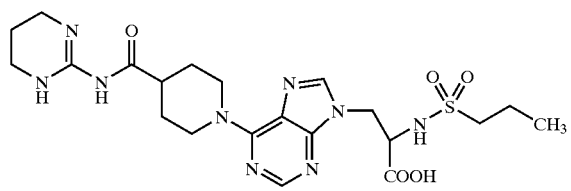

(2S)-2-(n-Propane-1-sulfonylamino)-3-(6-(4-(1,4,5,6-tetrahydropyrimidin-2-ylcarbamoyl)-piperidin-1-yl)-purin-9yl)-propionic acid tert-butyl ester The synthesis was carried out analogously to example 1e) using the compound of example 1, step d) and propane-1-sulfonyl chloride. Yield: 10%

MS (FAB): m/e=578.4 (100%, (M+H)$^+$); 522.4 (40%).

b) (2S)-2-(n-Propane-1-sulfonylamino)-3-(6-(4-(1,4,5,6-tetrahydropyrimidin-2-ylcarbamoyl)-piperidin-1-yl)-purin-9-yl)-propionic acid The synthesis was carried out analogously to example 1f) using 7 mg of the compound of step a). Yield: 6.3 mg (TFA salt).

MS (ES$^+$): m/e=522.4 (15%, (M+H)$^+$); 342.8 (15%); 261.7 (100%).

Example 5

(2S)-3-(6-(4-(1,4,5,6-Tetrahydropyrimidin-2-ylcarbamoyl)-piperidin-1-yl)-purin-9-yl)-2-(4-trifluoromethyl-benzenesulfonylamino)-propionic acid

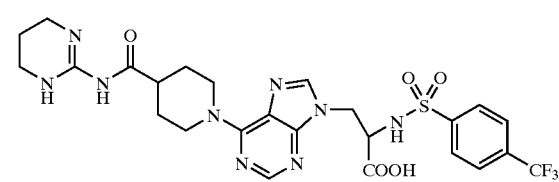

a) (2S)-3-(6-(4-(1,4,5,6-Tetrahydropyrimidin-2-ylcarbamoyl)-piperidin-1-yl)-purin-9-yl)-2-(4-trifluoromethyl-benzenesulfonylamino)-propionic acid tert-butyl ester The synthesis was carried out analogously to example 1e) using the compound of example 1, step d) and 4-trifluoromethyl-benzenesulfonyl chloride. Yield: 67%.

MS (ES): m/e=680.5 (10%, (M+H)$^+$); 340.9 (100%).

b) (2S)-3-(6-(4-(1,4,5,6-Tetrahydropyrimidin-2-ylcarbamoyl)-piperidin-1-yl)-purin-9-yl)-2-(4-trifluoromethyl-benzenesulfonylamino)-propionic acid The synthesis was carried out analogously to example 1f) using 60 mg of the compound of step a). Yield: 53 mg (TFA salt).

MS (ES+): m/e=624.4 (10%, (M+H)+); 333.3 (15%); 312.8 (100%).

Example 6

(2S)-3-(6-(4-(1,4,5,6-Tetrahydropyrimidin-2-ylcarbamoyl)-piperidin-1-yl)-purin-9-yl)-2-(3-trifluoromethyl-benzenesulfonylamino)-propionic acid

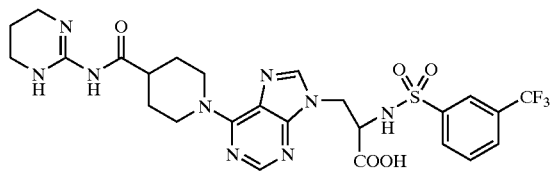

a) (2S)-3-(6-(4-(1,4,5,6-Tetrahydropyrimidin-2-ylcarbamoyl)-piperidin-1-yl)-purin-9-yl)-2-(3-trifluoromethyl-benzenesulfonylamino)-propionic acid tert-butyl ester The synthesis was carried out analogously to example 1e) using the compound of example 1, step d) and 3-trifluoromethyl-benzenesulfonyl chloride. Yield: 61%.

MS (ES+): m/e=680.5 (10%, (M+H)+); 340.9 (100%).

b) (2S)-3-(6-(4-(1,4,5,6-Tetrahydropyrimidin-2-ylcarbamoyl)-piperidin-1-yl)-purin-9-yl)-2-(3-trifluoromethyl-benzenesulfonylamino)-propionic acid The synthesis was carried out analogously to example 1f) using 55 mg of the compound of step a). Yield: 40 mg (TFA salt).

MS (ES+): m/e=624.4 (10%, (M+H)+); 333.3 (15%); 312.8 (100%).

Example 7

(2S)-2-Phenylmethanesulfonylamino-3-(6-(4-(1,4,5,6-tetrahydropyrimidin-2-ylcarbamoyl)-piperidin-1-yl)-purin-9-yl)-propionic acid

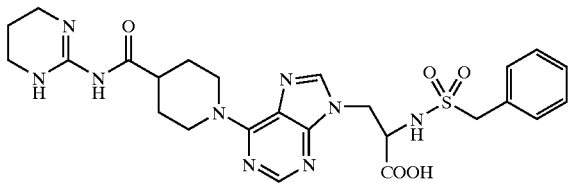

a) (2S)-2-Phenylmethanesulfonylamino-3-(6-(4-(1,4,5,6-tetrahydropyrimidin-2-ylcarbamoyl)-piperidin-1-yl)-purin-9-yl)-propionic acid tert-butyl ester The synthesis was carried out analogously to example 1e) using the compound of example 1, step d) and phenyl-methanesulfonyl chloride. Yield: 26%.

MS (ES+): m/e=626.5 (10%, (M+H)+); 313.9 (45%); 285.8 (100%).

b) (2S)-2-Phenylmethanesulfonylamino-3-(6-(4-(1,4,5,6-tetrahydropyrimidin-2-ylcarbamoyl)-piperidin-1-yl)-purin-9-yl)-propionic acid The synthesis was carried out analogously to example 1f) using 55 mg of the compound of step a). Yield: 40 mg (TFA salt).

MS (FAB): m/e=570.3 (100%, (M+H)+).

Example 8

(2S)-3-(6-(4-(1,4,5,6-Tetrahydropyrimidin-2-ylcarbamoyl)-piperidin-1-yl)-purin-9-yl)-2-trifluoromethanesulfonylamino-propionic acid

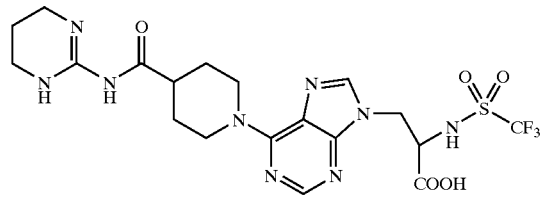

a) (2S)-3-(6-(4-(1,4,5,6-Tetrahydropyrimidin-2-ylcarbamoyl)-piperidin-1-yl)-purin-9-yl)-2-trifluoromethanesulfonylamino-propionic acid tert-butylester To 53.2 mg (0.1 mmol) of the compound of example 1d) in 1 ml of absolute DCM were added at −70° C. 56.5 mg (0.2 mmol) of trifluoromethansufonic acid anhydride in 0.5 ml of absolute DCM followed by 38.8 mg (0.3 mmol) of N,N-diisopropylethylamine in 0.5 ml of absolute DCM. The mixture was stirred at −70° C. for 1 h, then slowly warmed to 0° C. and stirred at 0° C. for 2 h. The solvent was removed in vacuo, the residue was dissolved in EE and the solution was extracted with aqueous NaHCO3 solution and brine, dried over MgSO4, filtered and the solvent was removed in vacuo. The crude product was purified by flash chromatography on silica gel (DCM/MeOH/AcOH/H2O (94:6:0.6:0.6)). Yield: 29.2 mg.

MS (ES+): m/e=604.5 (20%, (M+H)+); 323.4 (10%); 302.8 (100%), 274.8 (45%).

b) (2S)-3-(6-(4-(1,4,5,6-Tetrahydropyrimidin-2-ylcarbamoyl)-piperidin-1-yl)-purin-9yl)-2-trifluoromethanesulfonylamino-propionic acid The synthesis was carried out analogously to example 1f) using 29 mg of the compound of step a). Yield: 26 mg (TFA salt).

MS (FAB): m/e 548.1 (100%, (M+H)+).

Example 9

(2S)-3-(6-(4-(1,4,5,6-Tetrahydropyrimidin-2-ylcarbamoyl)-piperidin-1-yl)-purin-9-yl)-2-(2,2,2-trifluoro-ethanesulfonylamino)-propionic acid

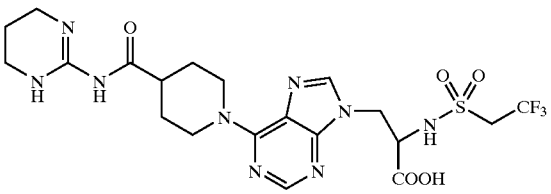

a) (2S)-3-(6-(4-(1,4,5,6-Tetrahydropyrimidin-2-ylcarbamoyl)-piperidin-1-yl)-purin-9-yl)-2-(2,2,2-trifluoro-ethanesulfonylamino)-propionic acid tert-butyl ester The synthesis was carried out analogously to example 1e) using the compound of example 1, step d) and 2,2,2-trifluoro-ethanesulfonyl chloride. Yield: 75%.

MS (ES+): m/e=618.2 (40%, (M+H)+); 330.2 (15%); 309.7 (100%), 281.6 (40%).

b) (2S)-3-(6-(4-(1,4,5,6-Tetrahydropyrimidin-2-ylcarbamoyl)-piperidin-1-yl)-purin-9-yl)-2-(2,2,2-trifluoro-ethanesulfonylamino)-propionic acid The synthesis was carried out analogously to example 1 q using 72 mg of the compound of step a). Yield: 68 mg (TFA salt).

MS (ES⁺): m/e=562.1 (8%, (M+H)⁺); 302.1 (10%); 281.6 (100%).

Example 10

(2S)-2-(2-Methylpropane-1-sulfonylamino)-3-(6-(4-(1,4,5,6-tetrahydropyrimidin-2-ylcarbamoyl)-piperidin-1-yl)-purin-9-yl)-propionic acid

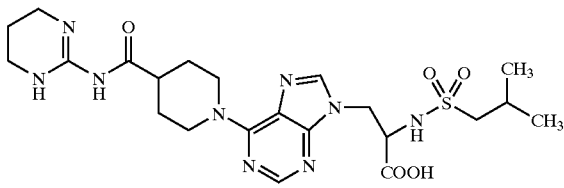

a) 1-(9-((2S)-2-Amino-2-tert-butoxycarbonyl-ethyl)-purin-6-yl)-piperidine-4-carboxylic acid 1.7 g of the compound of example 1b) in 200 ml of AcOH were hydrogenated over palladium/charcoal (10%) for 40 min at room temperature. The catalyst was filtered off, the solvent was removed in vacuo and the product was lyophylized. Yield: 1.28 g.

b) 1-(9-((2S)-2-tert-Butoxycarbonyl-2-(2-methyl-propane-1-sulfonylamino)-ethyl)-purin-6-yl)-piperidine-4-carboxylic add To 160 mg (0.41 mmol) of the compound of step a) in 2 ml of DMF were added 3 equivalents of N,O-bis-trimethylsilylacetamide and the mixture was stirred for 30 minutes at 0° C. and then for 30 minutes at room temperature. 64 mg (0.41 mmol) of 2-methyl-propane-1-sulfonyl chloride were added at 0° C. and the mixture was slowly brought to room temperature and stirred for 2 h. The solvent was removed in vacuo and the crude product was purified by silica gel chromatography (DCM/MeOH/AcOH/H₂O (95:5:0.5:0.5)). Yield: 80 mg (38%).

MS (ES⁺): m/e=511.3 (100%, (M+H)⁺); 467.3 (10%).

c) (2S)-2-(2-Methyl-propane-1-sulfonylamino)-3-(6-(4-(1,4,5,6-tetrahydropyrimidin-2-ylcarbamoyl)-piperidin-1-yl)-purin-9-yl)-propionic acid tert-butyl ester 80 mg (0.157 mmol) of the compound of step b) were dissolved in 2 ml of acetonitrile and treated with 35 mg of N,N'-dicyclohexylcarbodiimide and 29 mg of pentafluorophenol. The mixture was stirred for 30 minutes at room temperature, and the solvent was removed in vacuo. The residue was taken up in 2 ml of DMF and 31 mg 2-amino-1,4,5,6-tetrahydropyrimidine were added. The mixture was stirred for 12 h at room temperature, the solvent was evaporated and the crude product was purified by silica gel chromatography (DCM/MeOH/AcOH/H₂O (95:5:0.5:0.5). Yield: 45 mg (49%).

MS (ES): m/e=592.5 (15%, (M+H)⁺); 268.8 (100%).

d) (2S)-2-(2-Methyl-propane-1-sulfonylamino)-3-(6-(4-(1,4,5,6-tetrahydropyrimidin-2-ylcarbamoyl)-piperidin-1-yl)-purin-9-yl)-propionic acid 45 mg (0.076 mmol) of the compound of step c) were dissolved in TFA/H₂O (95:5) and stirred at room temperature for 30 minutes. The solvent was removed in vacuo and the residue was lyophylized. Yield: 100% (TFA salt).

MS (ES⁺): m/e=536.3 (15%, (M+H)⁺); 268.7 (100%).

Example 11

(2S)-3-(6-(4-(1,4,5,6-Tetrahydropyrimidin-2-ylcarbamoyl)-piperidin-1-yl)-purin-9-yl)-2-(toluene-4-sulfonylamino)-propionic acid

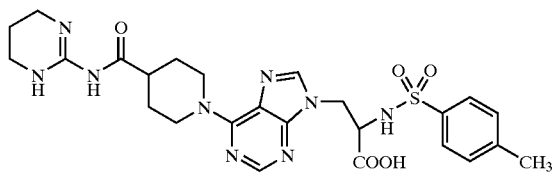

a) 1-(9-((2S)-2-tert-Butoxycarbonyl-2-(toluene-4-sulfonylamino)-ethyl)-purin-6-yl)-piperidine-4-carboxylic acid The synthesis was carried out analogously to example 10b) using the compound of example 10a) and toluene-4-sulfonyl chloride. Yield: 37%.

MS (ES⁺): m/e=545.2 (100%, (M+H)⁺); 489.1 (25%), 443.1 (15%).

b) (2S)-3-(6-(4-(1,4,5,6-Tetrahydropyrimidin-2-ylcarbamoyl)-piperidin-1-yl)-purin-9-yl)-2-toluene-4-sulfonylamino)-propionic acid tert-butyl ester The synthesis was carried out analogously to example 10c) using the compound of step a). Yield: 85%.

MS (FAB): m/e=626.3 (100%, (M+H)⁺); 570.2 (40%).

c) (2S)-3-(6-(4-(1,4,5,6-Tetrahydropyrimidin-2-ylcarbamoyl)-piperidin-1-yl)-purin-9-yl)-2-(toluene-4-sulfonylamino)-propionic acid The synthesis was carried out analogously to example 10d) using the compound of step b). Yield: 100% (TFA salt).

MS (FAB): m/e=570.3 (20%, (M+H)⁺); 285.7 (100%).

Example 12

(2S)-3-(6-(4-(1,4,5,6-Tetrahydropyrimidin-2-ylcarbamoyl)-piperidin-1-yl)-purin-9-yl)-2-(2,4,6-trimethyl-benzenesulfonylamino)-propionic acid

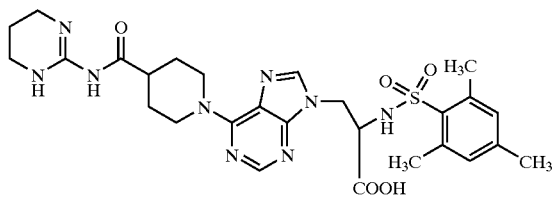

a) 1-(9-((2S)-2-tert-Butoxycarbonyl-2-(2,4,6-trimethyl-benzenesulfonylamino)-ethyl)-

The synthesis was carried out analogously to example 10b) using the compound of example 10a) and 2,4,6-trimethylbenzenesulfonyl chloride. Yield: 60%.

MS (FAB): m/e=573.4 (100%, (M+H)⁺).

b) (2S)-3-(6-(4-(1,4,5,6-Tetrahydropyrimidin-2-ylcarbamoyl)-piperidin-1-yl)-purin-9-yl)-2-(2,4,6-trimethyl/benzenesulfonylamino)-propionic acid tert-butyl ester The synthesis was carried out analogously to example 10c) using the compound of step a). Yield: 84%.

MS (FAB): m/e=654.5 (30%, (M+H)⁺); 327.8 (50%); 299.8 (100%).

c) (2S)-3-(6-(4-(1,4,5,6-Tetrahydropyrimidin-2-ylcarbamoyl)-piperidin-1-yl)-purin-9-yl)-2-(2,4,6-trimethyl-benzenesulfonylamino)-propionic acid The synthesis was carried out analogously to example 10d) using the compound of step b). Yield: 100% (TFA salt).

MS (FAB): m/e=598.4 (15%, (M+H)⁺); 299.8 (100%).

Pharmacological Testing

1) Kistrin Binding Assay

The inhibition of the binding of kistrin to human vitronectin receptor (VnR) described below is a test method by which the antagonistic action of the compounds of the invention on the vitronectin receptor $\alpha_v\beta_3$ can be determined ($\alpha_v\beta_3$ ELISA Test; the test method is abbreviated as "K/VnR" in the listing of the test results).

Purification of Kistrin

Kistrin is purified according to the methods of Dennis et al., as described in Proc. Natl. Acad. Sci. USA 87 (1989) 2471 and Proteins: Structure, Function and Genetics 15 (1993) 312.

Purification of Human Vitronectin Receptor ($\alpha_v\beta_3$)

Human vitronectin receptor is obtained from the human placenta according to the method of Pytela et al., Methods Enzymol. 144 (1987) 475. Human vitronectin receptor $\alpha_v\beta_3$ can also be obtained from some cell lines (for example from 293 cells, a human embryonic kidney cell line) which are co-transfected with DNA sequences for both subunits $\alpha_v$ and $\beta_3$ of the vitronectin receptor. The subunits are extracted with octyl glycoside and then chromatographed through concanavalin A, heparin-Sepharose and S-300.

Monoclonal Antibodies

Murine monoclonal antibodies which are specific for the $\beta_3$ subunits of the vitronectin receptor, are prepared according to the method of Newman et al., Blood, 1985, 227, or by a similar process. The rabbit Fab 2 anti-mouse Fc conjugate to horseradish peroxidase (anti-mouse Fc HRP) was obtained from Pel Freeze (Catalog No. 715 305-1).

ELISA Test

The ability of substances to inhibit the binding of kistrin to the vitronectin receptor can be determined using an ELISA test. For this purpose, Nunc 96-well microtiter plates are coated with a solution of kistrin (0.002 mg/ml) according to the method of Dennis et al., as described in Proteins: Structure, Function and Genetics 15 (1993) 312. The plates are then washed twice with PBS/0.05% Tween-20 and blocked by incubating (60 min) with bovine serum albumin (BSA, 0.5%, RIA grade or better) in buffer solution (Tris-HCl (50 mM), NaCl (100 mM), $MgCl_2$ (1 mM), $CaCl_2$ (1 mM), $MnCl_2$ (1 mM), pH 7). Solutions of known inhibitors and of the test substances are prepared in concentrations from $2\times10^{-12}$ to $2\times10^{-6}$ mol/l in assay buffer (BSA (0.5%, RIA grade or better); Tris-HCl (50 mM), NaCl (100 mM), $MgCl_2$ (1 mM), $CaCl_2$ (1 mM), $MnCl_2$ (1 mM), pH 7). The blocked plates are emptied, and in each case 0.025 ml of this solution which contains a defined concentration ($2\times10^{-12}$ to $2\times10^{-6}$ mol/l) either of a known inhibitor or of a test substance, are added to each well. 0.025 ml of a solution of the vitronectin receptor in assay buffer (0.03 mg/ml) is pipetted into each well of the plate and the plate is incubated at room temperature for 60–180 min on a shaker. In the meantime, a solution (6 ml/plate) of a murine monoclonal antibody specific for the $\beta_3$ subunit of the vitronectin receptor is prepared in assay buffer (0.0015 mg/ml). A second rabbit antibody (0.001 ml of stock solution/6 ml of the murine monoclonal anti-$\beta_3$ antibody solution) which is an anti-mouse Fc HRP antibody conjugate is added to this solution, and this mixture of murine anti-$\beta_3$ antibody and rabbit anti-mouse Fc HRP antibody conjugate is incubated during the time of the receptor-inhibitor incubation. The test plates are washed four times with PBS solution which contains 0.05% Tween-20, and in each case 0.05 ml/well of the antibody mixture is pipetted into each well of the plate and incubated for 60–180 min. The plate is washed four times with PBS/0.05% Tween-20 and then developed with 0.05 ml/well of a PBS solution which contains 0.67 mg/ml of o-phenylenediamine and 0.012% of $H_2O_2$. Alternatively to this, o-phenylenediamine can be employed in a buffer (pH 5) which contains $Na_3PO_4$ and citric acid. The color development is stopped using 1 N $H_2SO_4$ (0.05 ml/well). The absorption for each well is measured at 492–405 nm and the data are evaluated by standard methods.

2) Vitronectin/293 Cell Test

In this test the inhibition of binding of 293 cells to human vitronectin (Vn) by the compounds of the invention is determined (the test method is abbreviated as Vn/293 cell test in the listing of the test results).

Purification of Human Vitronectin

Human vitronectin was isolated from human plasma and purified by affinity chromatography according to the method of Yatohgo et al., Cell Structure and Function 23 (1988) 281.

Cell Test 293 cells, a human embryonic kidney cell line, which were cotransfected with DNA sequences for the $\alpha_v$ and $\beta_3$ subunits of the vitronectin receptor $\alpha_v\beta_3$, were selected for a high rate of expression (>500,000 $\alpha_v\beta_3$ receptors/cell) according to the FACS method. The selected cells were cultured and sorted again by means of FACS in order to obtain a stable cell line (15 D) with expression rates>1,000,000 copies of $\alpha_v\beta_3$ per cell.

A Linbro 96-well tissue culture plate with a flat bottom was coated overnight at 4° C. with human vitronectin (0.01 mg/ml, 0.05 ml/well) in phosphate-buffered saline solution (PBS) and then blocked with 0.5% strength BSA (bovine serum albumin). Solutions of the test substances from $10^{-10}$ mol/l to $2\times10^{-3}$ mol/l in glucose-containing DMEM medium were prepared and 0.05 ml/well of the solution were added to the plate in each case. The cells which expressed high levels of $\alpha_v\beta_3$ (for example 15 D) were suspended in glucose-containing DMEM medium and the suspension was adjusted to a content of 25,000 cells/0.05 ml of medium. 0.05 ml of this cell suspension was added to each well and the plate was incubated at 37° C. for 90 min. The plate was washed 3 times with warm PBS in order to remove unbound cells. The bound cells were lyzed in citrate buffer (25 mM, pH 5.0) which contained 0.25% Triton X-100. The hexoseamidase substrate p-nitrophenyl-N-acetyl-$\beta$-D-glucosaminide was then added and the plate was incubated at 37° C. for 90 min. The reaction was stopped with a glycine (50 mM)/EDTA (5 mM) buffer (pH 10.4) and the absorption of each well was measured at 405 to 650 nm. The data were analyzed according to standard methods.

3) Pit Assay

The inhibition of bone resorption by the compounds of the invention can be determined, for example, with the aid of an osteoclast resorption test ("Pit Assay"), for example analogously to WO-A-95/32710 which is incorporated herein by reference.

The following test results (inhibitory concentrations $IC_{50}$) were obtained.

| Compound | K/VnR $IC_{50}$ (nM) | Vn/293 cell test $IC_{50}$ (nM) | Pit Assay $IC_{50}$ (nM) |
| --- | --- | --- | --- |
| Example 1 | 1.9 | 30 | 0.8 |
| Example 2 | 2.5 | 9 | 2.3 |
| Example 3 | 4.5 | 67 | |
| Example 4 | 25 | 1400 | |
| Example 5 | 3.2 | 28 | 15 |
| Example 6 | 3.4 | 42 | |
| Example 7 | 23 | 500 | |

-continued

| Compound | K/VnR IC$_{50}$ (nM) | Vn/293 cell test IC$_{50}$ (nM) | Pit Assay IC$_{50}$ (nM) |
|---|---|---|---|
| Example 8 | 85 | | |
| Example 9 | 38 | 2500 | |
| Example 10 | 4.2 | 1120 | |
| Example 11 | 6.5 | 87 | |
| Example 12 | 5 | 38 | 26 |

What is claimed is:

1. A compound selected from the group consisting of a compound of the formula

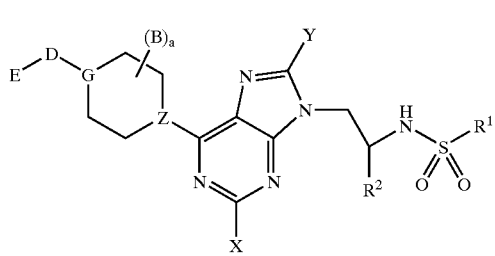

I wherein B is $(C_1–C_{18})$-alkyl, $(C_3–C_{14})$-cycloalkyl, $(C_3–C_{14})$-cycloalkyl-$(C_1–C_8)$-alkyl-, $(C_6–C_{14})$-aryl, $(C_6–C_{14})$-aryl-$(C_1–C_8)$-alkyl-, $(C_6–C_{14})$-heteroaryl, $(C_5–C_{14})$-heteroaryl-$(C_1–C_8)$-alkyl-, fluorine, chlorine, bromine, hydroxy, cyano, trifluoromethyl, nitro, hydroxy-carbonyl-, $(C_1–C_6)$-alkoxy, $(C_1–C_6)$-alkoxy-$(C_1–C_6)$-alkyl-, $(C_1–C_6)$-alkoxycarbonyl-, $(C_1–C_6)$-alkoxy-$(C_1–C_6)$-alkoxy-, $(C_5–C_{14})$-aryl-$(C_1–C_8)$-alkylcarbonyl-, $(C_1–C_6)$-alkanoylamino-, $(C_1–C_6)$-alkylsulfonylamino-, $(C_5–C_{14})$-arylsulfonylamino-, $(C_1–C_6)$-alkylamino-, di-$((C_1–C_6)$-alkyl)-amino-, $(C_1–C_6)$-alkylsulfonyl-, aminosulfonyl-, $(C_5–C_{14})$-arylsulfonyl-, $(C_5–C_{14})$-aryl-$(C_1–C_8)$-alkylsulfonyl-, $(C_6–C_{14})$-aryl and $(C_5–C_{14})$-heteroaryl, where all residues B are independent of one another, D is selected from the group consisting of —C(O)—N(R$^6$)—, —NR$^6$—C—(O)—, —NR$^6$—C(O)—N(R$^6$)—, —NR$^6$—C(S)—N(R$^6$)—, —C(S)—N(R$^6$)— or —C(R$^6$)=N—N(R$^6$)—, where the divalent Ds are bonded to E via the free bond on their right side;

E is selected from the group consisting of

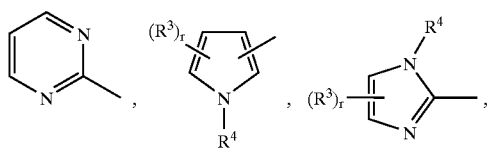

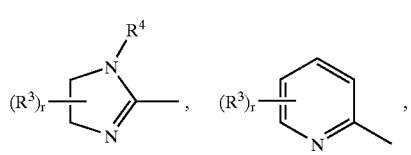

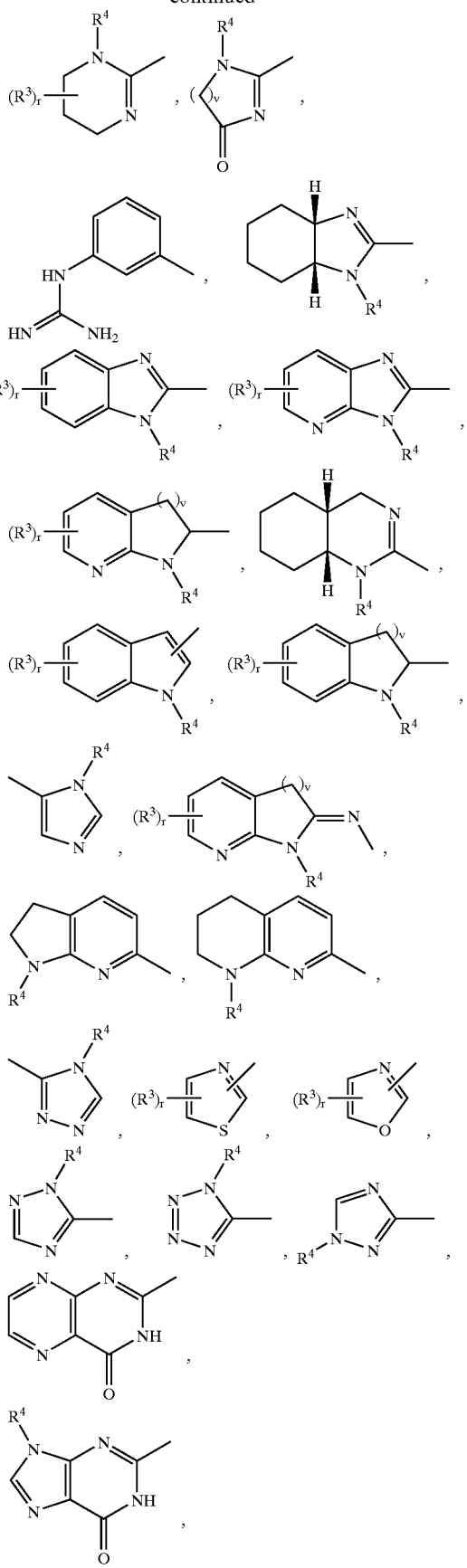

-continued

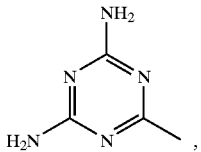

$R^6$—C(=NR$^6$)—NR$^6$— and R$^6$R$^{6'}$N—C(=NR$^6$)—;

G is selected from the group consisting of N, CH and C((C$_1$–C$_4$)-alkyl);

X is selected from the group consisting of hydrogen, —NR$^6$R$^{6'}$, fluorine, chlorine, bromine, —OR$^6$, —SR$^6$, hydroxy-(C$_1$–C$_6$)-alkyl-NH—, (hydroxy-(C$_1$–C$_6$)-alkyl)$_2$N—, amino-(C$_1$–C$_6$)-alkyl-NH—, (amino-(C$_1$–C$_6$)-alkyl)$_2$N—, hydroxy-(C$_1$–C$_6$)-alkyl-S— and —NH—C(O)—R$^6$;

Y is selected from the group consisting of R$^6$, fluorine, chlorine, bromine, cyano, —NR$^6$—R$^{6'}$, —OR$^6$, —SR$^6$ and hydroxy-(C$_1$–C$_6$)-alkyl-NH—;

Z is N or CH;

R$^1$ is selected from the group consisting of (C$_1$–C$_{18}$)-alkyl, (C$_3$–C$_{14}$)-cycloalkyl, (C$_3$–C$_{14}$)-cycloalkyl-(C$_1$–C$_8$)-alkyl-, (C$_6$–C$_{14}$)-aryl, (C$_6$–C$_{14}$)-aryl-(C$_1$–C$_8$)-alkyl-, (C$_5$–C$_{14}$)-heteroaryl or (C$_5$–C$_{14}$)-heteroaryl-(C$_1$–C$_8$)-alkyl- where aryl, heteroaryl, cycloalkyl and alkyl can be substituted one, two or three times by at least one member of the group consisting of fluorine, chlorine, bromine, cyano, trifluoromethyl, nitro, hydroxycarbonyl-, (C$_1$–C$_6$)-alkyl, (C$_1$–C$_6$)-alkoxy, (C$_1$–C$_6$)-alkoxy-(C$_1$–C$_6$)-alkyl-, (C$_1$–C$_6$)-alkoxycarbonyl-, (C$_1$–C$_6$)-alkylcarbonyl-, (C$_1$–C$_6$)-alkylaminocarbonyl-, (C$_1$–C$_6$)-alkoxy-(C$_1$–C$_6$)-alkoxy-, (C$_6$–C$_{14}$)-arylcarbonyl-, (C$_6$–C$_{14}$)-aryl-(C$_1$–C$_8$)-alkylcarbonyl-, (C$_1$–C$_6$)-alkanoylamino-, (C$_6$–C$_{14}$)-arylsulfonylamino-, (C$_1$–C$_6$)-alkylsulfonylamino-, (C$_1$–C$_6$)-alkylamino-, di-((C$_1$–C$_6$)-alkyl)-amino-, (C$_1$–C$_6$)-alkylsulfonyl-, (C$_1$–C$_6$)-alkylaminosulfonyl-, (C$_6$–C$_{14}$)-arylaminosulfonyl-, (C$_6$–C$_{14}$)-aryl-(C$_1$–C$_8$)-alkylaminosulfonyl-, (C$_6$–C$_{14}$)-arylsulfonyl-, (C$_6$–C$_{14}$)-aryl-(C$_1$–C$_8$)-alkylsulfonyl-, (C$_6$–C$_{14}$)-aryl and (C$_5$–C$_{14}$)-heteroaryl;

R$^2$ is selected from the group consisting of —C(O)R$^5$, —C(S)R$^5$, —S(O)$_p$R$^5$, —P(O)R$^5$—R$^{5'}$ a 4-membered to 8-membered saturated or unsaturated heterocycle which contains 1, 2, 3 or 4 heteroatoms selected from the group consisting of nitrogen, oxygen and sulfur;

R$^3$ is selected from the group consisting of (C$_1$–C$_{18}$)-alkyl, (C$_3$–C$_{14}$)-cycloalkyl, (C$_3$–C$_{14}$)-cycloalkyl-(C$_1$–C$_8$)-alkyl-, (C$_6$–C$_{14}$)-aryl, (C$_6$–C$_{14}$)-aryl-(C$_1$–C$_8$)-alkyl-, (C$_6$–C$_{14}$)-heteroaryl, (C$_6$–C$_{14}$)-heteroaryl-(C$_1$–C$_8$)-alkyl-, fluorine, chlorine, bromine, hydroxy, cyano, trifluoromethyl, nitro, hydroxycarbonyl-, (C$_1$–C$_6$)-alkoxy, (C$_1$–C$_6$)-alkoxy-(C$_1$–C$_6$)-alkyl-, (C$_1$–C$_6$)-alkoxycarbonyl-, (C$_1$–C$_6$)-alkyl-carbonyl-, (C$_5$–C$_{14}$)-arylcarbonyl-, (C$_1$–C$_6$)-alkylaminocarbonyl-, (C$_1$–C$_6$)-alkoxy-(C$_1$–C$_6$)-alkoxy-, (C$_6$–C$_{14}$)-aryl-(C$_1$–C$_8$)-alkylcarbonyl-, (C$_1$–C$_6$)-alkanoylamino-, (C$_1$–C$_6$)-alkylsulfonylamino-, (C$_6$–C$_{14}$)-arylsulfonylamino-, (C$_1$–C$_6$)-alkylamino-, di(C$_1$–C$_6$)-alkyl)amino-, (C$_1$–C$_6$)-alkylsulfonyl-, aminosulfonyl-, (C$_6$–C$_{14}$)-arylsulfonyl-, (C$_6$–C$_{14}$)-aryl-(C$_1$–C$_8$)-alkylsulfonyl-, (C$_6$–C$_{14}$)-aryl and (C$_5$–C$_{14}$)-heteroaryl, where alkyl R$^3$s are independent of one another;

R$^4$ is selected from the group consisting of hydrogen, (C$_1$–C$_{10}$)-alkyl, (C$_3$–C$_{14}$)-cycloalkyl, (C$_3$–C$_{14}$)-cycloalkyl, (C$_3$–C$_{14}$)-cycloalkyl-(C$_1$–C$_8$)-alkyl-, (C$_6$–C$_{14}$)-aryl and (C$_6$–C$_{14}$)-aryl-(C$_1$–C$_8$)-alkyl-;

R$^5$ and R$^{5'}$— are individually selected from the group consisting of hydroxy, (C$_1$–C$_8$)-alkoxy, (C$_6$–C$_{14}$)-aryl-(C$_1$–C$_8$)-alkoxy-, (C$_1$–C$_8$)-alkylcarbonyloxy-(C$_1$–C$_4$)-alkoxy-, (C$_6$–C$_{14}$)-aryl-(C$_1$–C$_8$)-alkylcarbonyloxy-(C$_1$–C$_8$)-alkoxy- and NR$^6$R$^{6'}$, where R$^5$ and R$^{5'}$ are independent of one another;

R$^6$ and R$^6$ are individually selected from the group consisting of hydrogen, (C$_1$–C$_{18}$)-alkyl, (C$_3$–C$_{14}$)-cycloalkyl, (C$_3$–C$_{14}$)-cycloalkyl-(C$_1$–C$_8$)-alkyl-, (C$_6$–C$_{14}$)-aryl where in the aryl, one, two, three, four or five ring carbon atoms can be replaced by heteroatoms selected from the group consisting of nitrogen, oxygen and sulfur, and (C$_6$–C$_{14}$)-aryl-(C$_1$–C$_8$)-alkyl- where in the aryl of the aryl-alkyl-, one, two, three, four or five ring carbon atoms can be replaced by heteroatoms selected from the group consisting of nitrogen, oxygen and sulfur, or R$^6$ and R$^{6'}$ together with the nitrogen atom to which they are bonded form a 4-membered to 8-membered ring system which in addition to the nitrogen atom to which R$^6$ and R$^{6'}$ are bonded can contain one, two or three ring heteroatoms selected from the group consisting of nitrogen, oxygen and sulfur and which can be unsaturated or saturated, where all R$^6$ and R$^{6'}$ are independent of one another;

r is zero;

s is zero, one, two, three or four;

v is one, two or three; and p is one or two;

in all their stereoisomeric forms and mixtures thereof in all ratios, and their non-toxic, physiologically tolerable salts.

2. A compound of claim 1 wherein B is (C$_1$–C$_{18}$)-alkyl or hydroxy, and all Bs are independent of one another, D is —C(O)—N(R$^6$)—, bonded to the group E via its nitrogen atom;

E is selected from the group consisting of

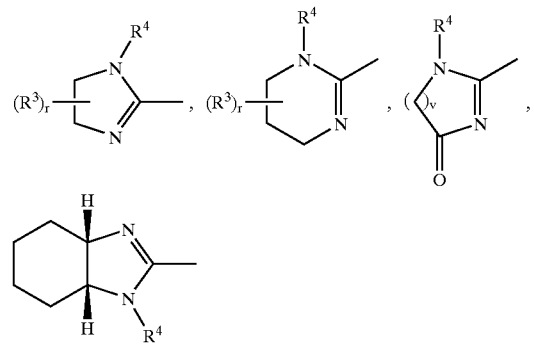

and R$^6$R$^{6'}$N—C(=NR$^6$)—;

G is N or CH;

X is hydrogen;

Y is hydrogen;

Z is N or CH;

R$^1$ is selected from the group consisting of (C$_1$–C$_{18}$)-alkyl, (C$_3$–C$_{14}$)-cycloalkyl, (C$_3$–C$_{14}$)-cycloalkyl, (C$_3$–C$_{14}$)-cycloalkyl-(C$_1$C$_8$)-alkyl-, (C$_6$–C$_{14}$)-aryl, (C$_6$–C$_{14}$)-aryl-(C$_1$–C$_8$)-alkyl-, (C$_5$–C$_{14}$)-heteroaryl and ($C_5$–$C_{14}$)-heteroaryl-($C_1$–$C_8$)-alkyl- where aryl, heteroaryl, cycloalkyl and alkyl can be substituted one, two or three times by at least one member selected from the group consisting of fluorine, chlorine, bromine, cyano, trifluoromethyl, nitro, hydroxycarbonyl-, ($C_1$–$C_6$)-alkyl, ($C_1$–$C_6$)-alkoxy, ($C_1$–$C_6$)-alkoxy-($C_1$–$C_6$)-alkyl, ($C_1$–$C_6$)-alkoxycarbonyl-, ($C_1$–$C_6$)-alkylcarbonyl-, ($C_1$–$C_6$)-alkylaminocarbonyl-, ($C_1$–$C_6$)-alkoxy-($C_1$–$C_6$)-alkoxy-($C_1$–$C_6$)-alkoxy-, ($C_6$–$C_4$)-arylcarbonyl-, ($C_6$–$C_{14}$)-aryl-($C_1$–$C_8$)-alkylcarbonyl-, ($C_1$–$C_6$)-alkanoylamino-, ($C_6$–$C_{14}$)-arylsulfonylamino-, ($C_1$–$C_6$)-alkylsulfonylamino-, ($C_1$–$C_6$)-alkylamino-, di-(($C_1$–$C_6$)-alkyl)amino-, ($C_1$–$C_6$)-alkylsulfonyl-, ($C_1$–$C_6$)-alkylaminosulfonyl-, ($C_6$–$C_{14}$)-arylsulfonyl-, ($C_6$–$C_{14}$)-aryl-($C_1$–$C_8$)-alkylsulfonyl-, ($C_6$–$C_{14}$)-aryl and ($C_5$–$C_{14}$)-heteroaryl;

$R^1$ is —C(O)$R^5$;

$R^3$ is selected from the group consisting of ($C_1$–$C_6$)-alkyl, ($C_3$–$C_{14}$)-cycloalkyl, ($C_3$–$C_{14}$)-cycloalkyl-($C_1$–$C_8$)-alkyl-, fluorine, chlorine, bromine, cyano, trifluoromethyl, hydroxy or ($C_1$–$C_6$)-alkoxy, where all $R^3$s are independent of one another;

$R^4$ is hydrogen or ($C_1$–$C_6$)-alkyl;

$R^5$ is hydroxy or ($C_1$–$C_8$)-alkoxy;

$R^6$ and $R^{6'}$ are selected from the group consisting of hydrogen, ($C_1$–$C_6$)-alkyl, ($C_3$–$C_{14}$)-cycloalkyl, ($C_3$–$C_{14}$)-cycloalkyl-($C_1$–$C_8$)-alkyl-, ($C_6$–$C_{14}$)-aryl where in the aryl, one, two or three ring carbon atoms can be replaced by heteroatoms selected from the group consisting of nitrogen, oxygen and sulfur, and ($C_6$–$C_{14}$)-aryl-($C_1$–$C_8$)-alkyl- where in the aryl of the aryl-alkyl-, one, two or three ring carbon atoms can be replaced by heteroatoms selected from the group consisting of nitrogen, oxygen and sulfur, or $R^6$ and $R^{6'}$ together with the nitrogen atom to which they are bonded form a 4-membered to 6-membered ring system which in addition to the nitrogen atom to which $R^6$ and $R^{6'}$ are bonded can contain one, two or three ring heteroatoms selected from the group consisting of nitrogen, oxygen and sulfur and which can be unsaturated or saturated, where all $R^6$ and $R^{6'}$s are independent of one another;

r is zero, one, two, three or four;

s is zero, one, two, three or four;

v is one, two or three;

in all their stereoisomeric forms and mixtures thereof in all ratios, and their non-toxic physiologically tolerable salts.

3. A compound of claim 1 wherein B is ($C_1$–$C_6$)-alkyl or hydroxy, where all Bs are independent of one another;

D is (O)—N($R^6$)—, bonded to the group E via its nitrogen atom;

E is selected from the group consisting of

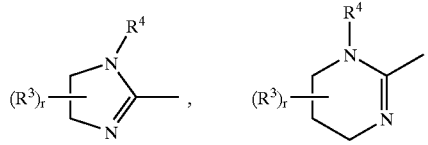

G is N or CH;

X is hydrogen;

Y is hydrogen;

Z is N;

$R^1$ is selected from the group consisting of ($C_1$–$C_{18}$)-alkyl, ($C_3$–$C_{14}$)-cycloalkyl, ($C_3$–$C_{14}$)-cycloalkyl-($C_1$–$C_8$)-alkyl-, ($C_6$–$C_{14}$)-aryl, ($C_1$–$C_8$)-alkyl-, ($C_5$–$C_{14}$)-heteroaryl and ($C_5$–$C_{14}$)-heteroaryl-($C_1$–$C_8$)-alkyl- where aryl, heteroaryl, cycloalkyl and alkyl can be substituted one, two or three times by at least one member of the group consisting of fluorine, chlorine, bromine, cyano, trifluoromethyl, nitro, hydroxycarbonyl-, ($C_1$–$C_6$)-alkyl, ($C_1$–$C_6$)-alkoxy, ($C_1$–$C_6$)-alkoxy-($C_1$–$C_6$)-alkyl-, ($C_1$–$C_6$)-alkoxycarbonyl-, ($C_1$–$C_6$)-alkylcarbonyl-, ($C_1$–$C_6$)-alkylaminocarbonyl-, ($C_1$–$C_6$)-alkoxy-($C_1$–$C_6$)-alkoxy, ($C_6$–$C_{14}$)-arylcarbonyl-, ($C_6$–$C_{14}$)-aryl-($C_1$–$C_8$)-alkylcarbonyl-, ($C_1$–$C_6$)-alkanoylamino-, ($C_6$–$C_{14}$)-arylsulfonylamino-, ($C_1$–$C_6$)-alkylsulfonylamino-, ($C_1$–$C_6$)-alkylamino-, di-(($C_1$–$C_6$)-alkyl)amino-, ($C_1$–$C_6$)-alkylsulfonyl, ($C_1$–$C_6$)-alkylaminosulfonyl-, ($C_6$–$C_{14}$)-arylaminosulfonyl-, ($C_6$–$C_{14}$)-aryl-($C_1$–$C_8$)-alkylaminosulfonyl-, ($C_6$–$C_{14}$)-arylsulfonyl-, ($C_6$–$C_{14}$)-aryl-($C_1$–$C_8$)-alkylsulfonyl-, ($C_6$–$C_{14}$)-aryl and ($C_5$–$C_{14}$)-heteroaryl;

$R^2$ is —C(O)$R^5$;

$R^3$ is selected from the group consisting of ($C_1$–$C_6$)-alkyl, fluorine, chlorine, bromine, cyano, hydroxy and ($C_1$–$C_6$)-alkoxy, where all $R^3$s are independent of one another;

$R^4$ is hydrogen or ($C_1$–$C_4$)-alkyl;

$R^5$ is hydroxy or ($C_1$–$C_6$)-alkoxy;

$R^6$ and $R^{6'}$ are selected from the group consisting of hydrogen, ($C_1$–$C_6$)-alkyl, ($C_3$–$C_{14}$)-cycloalkyl, ($C_3$–$C_{14}$)-cycloalkyl-($C_1$–$C_8$)-alkyl and ($C_6$–$C_{14}$)-aryl-($C_1$–$C_8$)-alkyl-, or $R^6$ and $R^{6'}$ together with the nitrogen atom to which they are bonded form a 4-membered to 6-membered ring system which in addition to the nitrogen atom to which $R^6$ and $R^{6'}$ are bonded can contain one or two ring heteroatoms selected from the group consisting of nitrogen, oxygen and sulfur and which can be unsaturated or saturated, where all $R^6$ and $R^{6'}$ are independent of one another;

r is zero, one, two, three or four;

s is zero, one or two;

in all their stereoisomeric forms and mixtures thereof in all ratios, and their non-toxic physiologically tolerable salts.

4. A compound of claim 1 wherein D is —C(O)—N($R^6$)—, bonded to E via its nitrogen atom;

E is selected from the group consisting of

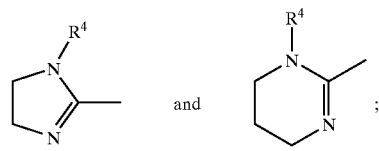

G is CH;

X is hydrogen;

Y is hydrogen;

Z is N;

$R^1$ is selected from the group consisting of ($C_1$–$C_{18}$)-alkyl, ($C_3$–$C_{14}$)-cycloalkyl-($C_1$–$C_8$)-alkyl-, ($C_6$–$C_{14}$)-aryl, ($C_6$–$C_{14}$)-aryl-($C_1$–$C_8$)-alkyl-, ($C_5$–$C_{14}$)- heteroaryl and $(C_5-C_{14})$-heteroaryl-$(C_1-C_8)$-alkyl- where aryl, heteroaryl, cycloalkyl and alkyl can be substituted one, two, or three times by at least one member of the group consisting of fluorine, chlorine, bromine, cyano, trifluoromethyl, nitro, hydroxycarbonyl-, $(C_1-C_6)$-alkyl, $(C_1-C_6)$-alkoxy, $(C_1-C_6)$-alkoxy-$(C_1-C_6)$-alkyl-, $(C_1-C_6)$-alkoxycarbonyl-, $(C_1-C_6)$-alkylcarbonyl-, $(C_1-C_6)$-alkylaminocarbonyl-, $(C_1-C_6)$-alkoxy-$(C_1-C_6)$-alkoxy-, $(C_6-C_{14})$-arylcarbonyl-, $(C_6-C_{14})$-aryl-$(C_1-C_8)$-alkylcarbonyl-, $(C_1-C_6)$-alkanoylamino-, $(C_6-C_{14})$-arylsulfonylamino-, $(C_1-C_6)$-alkylsulfonylamino-, $(C_1-C_6)$-alkylamino-, di-$(C_1-C_6)$-alkyl)amino-, $(C_1-C_6)$-alkylsulfonyl-, $(C_1-C_6)$-alkylaminosulfonyl-, $(C_5-C_{14})$-arylaminosulfonyl-, $(c_5-C_{14})$-aryl-$(C_1-C_8)$-alkylaminosulfonyl-, $(C_6-C_{14})$-arylsulfonyl-, $(C_6-C_{14})$-aryl-$(C_1-C_8)$-alkylsulfonyl-, $(C_6-C_{14})$-aryl and $(C_5-C_{14})$-heteroaryl;

$R^1$ is —C(O)$R^5$;
$R^4$ is hydrogen or $(C_1-C_4)$-alkyl;
$R^5$ is hydroxy or $(C_1-C_6)$-alkoxy;
$R^6$ is hydrogen or $(C_1-C_4)$-alkyl;
s is zero;

in all their stereoisomeric forms and mixtures thereof in all ratios, and their non-toxic, physiologically tolerable salts.

5. A compound of claim 1 wherein D is —C(O)—NH—, bonded to E via its nitrogen atom;

E is

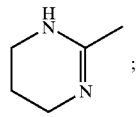

G is CH;
X is hydrogen;
Y is hydrogen;
Z is N;
$R^1$ is selected from the group consisting of $(C_1-C_{18})$-alkyl, $(C_3-C_{14})$-cycloalkyl-$(C_1-C_8)$-alkyl-, $(C_6-C_{14})$-aryl, $(C_6-C_{14})$-aryl-$(C_1-C_8)$-alkyl, $(C_5-C_{14})$-heteroaryl and $(C_5-C_{14})$-heteroaryl-$(C_1-C_8)$-alkyl- where aryl, heteroaryl, cycloalkyl and alkyl can be substituted one, two or three times by at least one member of the group consisting of fluorine, chlorine, bromine, cyano, trifluoromethyl, $(C_1-C_6)$-alkyl, $(C_1-C_6)$-alkoxy and $(C_5-C_{14})$-aryl;

$R^2$ is —C(O)$R^5$;
$R^5$ is hydroxy or $(C_1-C_6)$-alkoxy;
s is zero;

in all their stereoisomeric forms and mixtures thereof in all ratios, and their non-toxic, physiologically tolerable salts.

6. A process for the preparation of a compound of claim 1 comprising reacting a compound of the formula

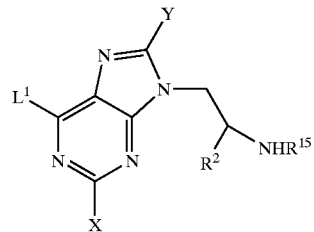

V with a compound of the formula VIa or with a compound of the formula VIB

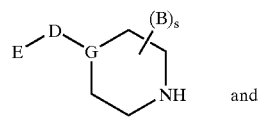

VIa and

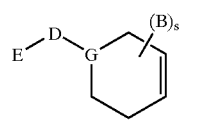

VIb wherein $L^1$ is a leaving group, $R^{15}$ is $R^1$—SO$_2$— or an amino protecting group and B, D, E, G, X, $R^2$ and s are defined as in claim 1 but where functional groups can also be present in the form of unprotected groups or in protected form.

7. A pharmaceutical composition, comprising a compound of claim 1 and a pharmaceutically acceptable carrier.

8. A method of treating osteoporosis in warm-blooded animals comprising administering to warm-blooded animals in need thereof an amount of a compound of claim 1 sufficient to treat osteoporosis.

* * * * *